United States Patent
Park et al.

(10) Patent No.: US 10,971,938 B2
(45) Date of Patent: Apr. 6, 2021

(54) ELECTRONIC DEVICE INCLUDING BIOSENSOR AND OPERATING METHOD THEREOF

(71) Applicant: Samsung Electronics Co., Ltd., Gyeonggi-do (KR)

(72) Inventors: Jongho Park, Seoul (KR); Inho Yun, Gyeonggi-do (KR); Doo-Suk Kang, Gyeonggi-do (KR); Jeong-Min Park, Gyeonggi-do (KR)

(73) Assignee: Samsung Electronics Co., Ltd

( * ) Notice: Subject to any disclaimer, the term of this patent is extended or adjusted under 35 U.S.C. 154(b) by 348 days.

(21) Appl. No.: 15/881,446

(22) Filed: Jan. 26, 2018

(65) Prior Publication Data
US 2018/0212449 A1    Jul. 26, 2018

(30) Foreign Application Priority Data
Jan. 26, 2017   (KR) .......................... 10-2017-0012521

(51) Int. Cl.
*H02J 7/00* (2006.01)
*A61B 5/0408* (2006.01)
(Continued)

(52) U.S. Cl.
CPC .............. *H02J 7/00* (2013.01); *A61B 5/0245* (2013.01); *A61B 5/04085* (2013.01);
(Continued)

(58) Field of Classification Search
CPC ... A61B 5/0245; A61B 5/681; A61B 5/02444; A61B 5/02; G06F 3/0346; G06F 3/011;
(Continued)

(56) References Cited

U.S. PATENT DOCUMENTS 4,513,753 A *  4/1985  Tabata ................. A61B 5/0404
                                                            600/519
4,746,809 A *  5/1988  Coleman .............. H05B 47/185
                                                            307/1
(Continued)

FOREIGN PATENT DOCUMENTS

CN        106170244        11/2016
JP        2012-019811       2/2012
(Continued)

OTHER PUBLICATIONS

International Search Report dated May 4, 2018 issued in counterpart application No. PCT/KR2018/000937, 8 pages.
(Continued)

*Primary Examiner* — John T Trischler
(74) *Attorney, Agent, or Firm* — The Farrell Law Firm, P.C.

(57) ABSTRACT

An electronic device that can be worn on a user's body and an operating method thereof. An electrode for charging and measuring is included in a front side of the electronic device. The electronic device includes a battery, a charging circuit for charging the battery, a bio-sensor, and a processor. The processor is configured to determine whether the battery is being charged through the charging circuit. If the battery is not being charged, the processor is configured to acquire biometric information by using a first method through the bio-sensor, and if the battery is being charged, the processor is configured to acquire the biometric information by using a second method through the bio-sensor.

12 Claims, 22 Drawing Sheets

(51) Int. Cl.
  *A61B 5/0245* (2006.01)
  *A61B 5/00* (2006.01)
  *G16H 50/00* (2018.01)
  *A61B 5/0205* (2006.01)

(52) U.S. Cl.
  CPC .......... *A61B 5/6898* (2013.01); *G16H 50/00* (2018.01); *H02J 7/0042* (2013.01); *A61B 5/0205* (2013.01); *A61B 5/681* (2013.01); *A61B 2560/029* (2013.01); *A61B 2560/0209* (2013.01); *A61B 2560/0214* (2013.01); *A61B 2562/0209* (2013.01)

(58) Field of Classification Search
  CPC .......... G06F 3/01; H02J 7/0042; H02J 7/025; H04N 5/2258; H01M 10/0431; H01M 10/44
  USPC ........................................... 320/114
  See application file for complete search history.

(56) References Cited

U.S. PATENT DOCUMENTS

| | | | | |
|---|---|---|---|---|
| 5,072,167 | A * | 12/1991 | Zias | H02J 7/0034 320/165 |
| 5,936,317 | A * | 8/1999 | Sasanouchi | H02J 9/005 307/10.7 |
| 8,155,368 | B2 * | 4/2012 | Cheung | H04R 5/0335 379/430 |
| 8,363,425 | B2 * | 1/2013 | Rupert | H01M 10/486 180/2.1 |
| 8,795,184 | B2 * | 8/2014 | Niwa | A61B 5/14551 600/481 |
| 8,954,099 | B2 * | 2/2015 | Forutanpour | G06F 1/1626 455/466 |
| D736,107 | S | 8/2015 | Lee | |
| 9,197,082 | B1 * | 11/2015 | Zhang | G16H 40/63 |
| 9,211,076 | B2 * | 12/2015 | Kim | A61B 5/0416 |
| 9,237,869 | B1 * | 1/2016 | Lee | A61B 5/6804 |
| 9,276,625 | B2 * | 3/2016 | Jing | H04M 1/0202 |
| 9,287,728 | B2 * | 3/2016 | Odaohhara | H01M 10/443 |
| D757,275 | S | 5/2016 | Lee | |
| 9,442,523 | B2 * | 9/2016 | Lee | G06F 1/163 |
| 9,484,736 | B2 * | 11/2016 | Hong | H02H 5/083 |
| 9,526,433 | B2 * | 12/2016 | Lapetina | A61B 5/04085 |
| 9,590,433 | B2 * | 3/2017 | Li | H04M 1/18 |
| 9,591,913 | B2 * | 3/2017 | Kim | G04B 37/084 |
| 9,594,404 | B2 * | 3/2017 | Yoon | G01R 33/07 |
| 9,629,574 | B2 * | 4/2017 | Lee | A61B 5/1118 |
| 9,768,628 | B2 * | 9/2017 | Fish | H02J 7/0042 |
| 9,861,280 | B2 * | 1/2018 | Lee | A61B 5/681 |
| 9,872,525 | B2 * | 1/2018 | Lee | A41D 1/002 |
| 9,872,619 | B2 * | 1/2018 | Lee | A61B 5/0006 |
| 9,874,457 | B2 * | 1/2018 | Fung | A61B 5/1118 |
| 9,883,730 | B2 * | 2/2018 | Lee | A45F 5/00 |
| 9,891,667 | B2 * | 2/2018 | Jung | G06F 1/1633 |
| 9,899,832 | B2 * | 2/2018 | Kuo | G06F 1/163 |
| 9,913,591 | B2 * | 3/2018 | Lapetina | A61B 5/6843 |
| 9,962,082 | B2 * | 5/2018 | Kim | A61B 5/6803 |
| 10,008,870 | B2 * | 6/2018 | Davison | H04B 1/3883 |
| 10,103,541 | B2 * | 10/2018 | Kuo | G06F 1/163 |
| 10,128,670 | B2 * | 11/2018 | Ban | H02J 7/0031 |
| 10,368,773 | B2 * | 8/2019 | Jung | A61B 5/7278 |
| 10,477,354 | B2 * | 11/2019 | Patel | A61B 5/681 |
| 10,532,181 | B2 * | 1/2020 | Hooper | A61M 21/02 |
| 10,585,467 | B2 * | 3/2020 | Moon | H02J 7/0034 |
| 2005/0196003 | A1 * | 9/2005 | Fluit | H02J 7/0034 381/323 |
| 2006/0229520 | A1 * | 10/2006 | Yamashita | A61B 5/0002 600/503 |
| 2007/0191719 | A1 | 8/2007 | Yamashita et al. | |
| 2008/0088280 | A1 * | 4/2008 | Wan | H02J 7/0031 320/136 |
| 2008/0171945 | A1 * | 7/2008 | Dotter | A61B 5/486 600/514 |
| 2009/0085514 | A1 * | 4/2009 | Mizoguchi | H02J 7/0042 320/113 |
| 2009/0163820 | A1 * | 6/2009 | Eerden | A61B 5/00 600/481 |
| 2009/0184687 | A1 * | 7/2009 | Schroeder | H02J 7/0071 320/162 |
| 2009/0274335 | A1 * | 11/2009 | Cheung | H04R 5/0335 381/374 |
| 2010/0089846 | A1 * | 4/2010 | Navarro Ruiz | B60L 53/36 211/4 |
| 2011/0050175 | A1 * | 3/2011 | Odaohhara | H01M 10/443 320/134 |
| 2011/0090666 | A1 * | 4/2011 | Rupert | H01M 10/486 361/829 |
| 2011/0215931 | A1 * | 9/2011 | Callsen | F41H 1/04 340/573.1 |
| 2011/0218756 | A1 * | 9/2011 | Callsen | F41H 1/04 702/139 |
| 2011/0312349 | A1 * | 12/2011 | Forutanpour | G06F 1/1626 455/466 |
| 2011/0316353 | A1 * | 12/2011 | Ichikawa | H02J 7/0044 307/149 |
| 2012/0022382 | A1 * | 1/2012 | Daisuke | A61B 5/14551 600/481 |
| 2012/0078071 | A1 * | 3/2012 | Bohm | G06F 1/3203 600/345 |
| 2013/0015824 | A1 * | 1/2013 | Newton | H02J 7/0034 320/165 |
| 2013/0020986 | A1 * | 1/2013 | Linzon | H02J 5/00 320/107 |
| 2013/0118255 | A1 * | 5/2013 | Callsen | A42B 3/046 73/491 |
| 2013/0211290 | A1 * | 8/2013 | Lee | A43B 3/0005 600/592 |
| 2013/0310677 | A1 * | 11/2013 | Chiu | A61B 5/021 600/384 |
| 2014/0152253 | A1 * | 6/2014 | Ozaki | H02J 5/005 320/108 |
| 2014/0239904 | A1 * | 8/2014 | Tanaka | B60R 16/04 320/128 |
| 2014/0247155 | A1 * | 9/2014 | Proud | A61B 5/1118 340/870.16 |
| 2014/0307356 | A1 * | 10/2014 | Hong | H02H 5/083 361/78 |
| 2014/0371611 | A1 * | 12/2014 | Kim | A61B 5/0416 600/509 |
| 2015/0137731 | A1 * | 5/2015 | Kim | H02J 7/35 320/101 |
| 2015/0162577 | A1 * | 6/2015 | Takano | H01M 2/1005 429/65 |
| 2015/0181324 | A1 * | 6/2015 | Hsieh | H04R 1/105 381/74 |
| 2015/0188347 | A1 * | 7/2015 | Ruan | H02J 7/0063 320/118 |
| 2015/0189976 | A1 * | 7/2015 | Lee | A45F 5/00 224/267 |
| 2015/0270734 | A1 * | 9/2015 | Davison | H02J 7/0044 320/103 |
| 2015/0340891 | A1 * | 11/2015 | Fish | H02J 7/342 320/103 |
| 2015/0345985 | A1 | 12/2015 | Fung et al. | |
| 2016/0026212 | A1 * | 1/2016 | Lee | G06F 1/163 361/679.03 |
| 2016/0045135 | A1 * | 2/2016 | Kim | A61B 5/6843 600/391 |
| 2016/0099613 | A1 * | 4/2016 | Bell | H02J 7/025 307/104 |
| 2016/0106337 | A1 * | 4/2016 | Jung | A61B 5/681 600/547 |
| 2016/0112775 | A1 * | 4/2016 | Kim | A61B 5/0002 340/870.07 |
| 2016/0120463 | A1 * | 5/2016 | Chen | A61B 5/02438 600/479 |
| 2016/0151007 | A1 * | 6/2016 | Tateda | A61B 5/00 600/476 |

(56) References Cited

U.S. PATENT DOCUMENTS

| | | | |
|---|---|---|---|
| 2016/0181840 A1* | 6/2016 | Kang | H02J 7/007 320/107 |
| 2016/0192716 A1* | 7/2016 | Lee | G06F 3/015 2/422 |
| 2016/0192856 A1* | 7/2016 | Lee | A61B 5/6804 600/384 |
| 2016/0192857 A1* | 7/2016 | Lee | A61B 5/681 600/382 |
| 2016/0206212 A1 | 7/2016 | Lee et al. | |
| 2016/0241059 A1* | 8/2016 | Li | H04M 1/18 |
| 2016/0255733 A1* | 9/2016 | Jung | G06F 1/1633 361/759 |
| 2016/0284961 A1* | 9/2016 | Alhawari | H01L 35/28 |
| 2016/0308583 A1* | 10/2016 | Hsu | H04B 5/0025 |
| 2016/0317067 A1* | 11/2016 | Lee | A61B 5/1118 |
| 2016/0346501 A1* | 12/2016 | Hooper | A61B 5/486 |
| 2016/0378069 A1* | 12/2016 | Rothkopf | G06F 1/1643 368/10 |
| 2016/0378070 A1* | 12/2016 | Rothkopf | G06F 1/1643 368/10 |
| 2016/0378071 A1* | 12/2016 | Rothkopf | G06F 1/1643 368/10 |
| 2017/0000415 A1 | 1/2017 | Lapetina et al. | |
| 2017/0054289 A1* | 2/2017 | Kuo | G06F 1/163 |
| 2017/0054290 A1* | 2/2017 | Di | H02J 7/00 |
| 2017/0054308 A1* | 2/2017 | Olah | H02J 7/32 |
| 2017/0063107 A1* | 3/2017 | Lee | G16H 40/67 |
| 2017/0063117 A1* | 3/2017 | Ban | G01R 27/22 |
| 2017/0085296 A1* | 3/2017 | Hsu | H04B 5/0031 |
| 2017/0150773 A1* | 6/2017 | Beers | A43C 11/008 |
| 2017/0172448 A1* | 6/2017 | Shin | A61B 5/0022 |
| 2017/0296088 A1* | 10/2017 | Choi | A61B 5/02055 |
| 2018/0028090 A1* | 2/2018 | Tremblay | A61B 5/04001 |
| 2018/0070840 A1* | 3/2018 | Cronin | A61B 5/6824 |
| 2018/0115179 A1* | 4/2018 | Fan | H02J 50/10 |
| 2018/0120892 A1* | 5/2018 | von Badinski | G06F 3/1423 |
| 2018/0235542 A1* | 8/2018 | Yun | A61B 5/0205 |
| 2018/0360326 A1* | 12/2018 | Lee | H01M 10/44 |
| 2019/0073009 A1* | 3/2019 | Moon | H01M 10/48 |
| 2020/0171269 A1* | 6/2020 | Hooper | A61M 21/02 |

FOREIGN PATENT DOCUMENTS

| | | |
|---|---|---|
| JP | 2016-101345 | 6/2016 |
| JP | 2016-144560 | 8/2016 |
| KR | 10-2015-0007586 | 1/2015 |
| KR | 10-2016-0044811 | 4/2016 |
| KR | 10-2016-0078711 | 7/2016 |
| KR | 1020160107839 | 9/2016 |
| WO | WO 2016/146652 | 9/2016 |

OTHER PUBLICATIONS

European Search Report dated Oct. 23, 2019 issued in counterpart application No. 18745084.6-1115, 8 pages.

Chinese Office Action dated Jun. 2, 2020 issued in counterpart application No. 201880007384.6, 21 pages.

Indian Examination Report dated Jan. 27, 2021 issued in counterpart application No. 201937029105, 6 pages.

\* cited by examiner

ELECTRONIC DEVICE INCLUDING BIOSENSOR AND OPERATING METHOD THEREOF

PRIORITY

This application claims priority under 35 U.S.C. § 119(a) to a Korean Patent Application filed in the Korean Intellectual Property Office on Jan. 26, 2017, and assigned Serial No. 10-2017-0012521, the entire content of which is incorporated herein by reference.

BACKGROUND

1. Field of the Disclosure

The present disclosure relates generally to an electronic device, and particularly to a wearable device that can be worn on a user's body and its operating method.

2. Description of Related Art

Recently, there has been an increase in the development and use of an electronic device (e.g., a wearable device) that can be worn on a part of a user's body. For example, due to the development of miniaturization techniques, electronic devices are capable of performing a more precise and advanced biometric measurement according to a wearable characteristic, and are increasingly used for a user's health care.

The electronic device may be a device capable of communicating with a user at a nearest location of a user's body, rather than simply worn on the user's body as an accessory. The electronic device has an advantage in that detailed information about a surrounding environment or a change in the user's body can be persistently collected on a real time basis. For example, the electronic device may include various sensors (e.g., an optic sensor, an acceleration sensor, an electrode sensor, etc.) for measuring a user's bio-signal, and may measure and provide a variety of biometric information such as a user's heartbeat, blood oxygen saturation (SpO2), step count, sleep state, stress information, body fat information, calorie consumption, and the like. A main purpose of such an electronic device may be to provide biometric information measured during a daily life, as well as biometric information measured during exercise, and thus a long time of usage is necessarily required. That is, it is important that the wearable electronic device has a long battery lifespan corresponding to a time required until it is recharged after being charged one time.

Therefore, the electronic device has recently been developed to improve a usage time to a specific duration (e.g., one week, etc.) by applying a low power sensor and a low power circuit design. According to a specific period of time or a user's requirement, the electronic device may be used in such a manner that charging is performed by separating it from a user's body. For example, although battery performance has been improved, the electronic device may necessarily require the charging despite of the improvement in the battery performance.

In general, an electronic device (e.g., a wrist wearable device) which can be worn on a user's body may include two additional electrodes or charging ports on a rear or lateral side to charge the electronic device. Therefore, the electronic device may have a limitation in that user's biometric information cannot be measured during charging because the electronic device must be separated from the user's body for charging.

For example, since the electronic device must be separated from a user's wrist for charging, the electronic device may not be able to acquire the user's health information during a charging time, which results in a problem in that continuity of the health information cannot be maintained. In addition, there is a problem in that accuracy of the health information deteriorates because a period of acquiring the health information must be set to be long in order to maximize a usage time after the electronic device is fully charged. In other words, the amount of operations or information that can be generated may vary depending on whether the electronic device is in a state of being worn on the user's body or a state of not being worn on the user's body. In a case of an electronic device which guarantees a battery time less than one day, it may be difficult to use it since a measurement is limited during sleep. Or in case of an electronic device which guarantees a battery time of a specific duration (e.g., 3 days or one week), a biometric measurement value or an activity measurement value may be missed for a time during which it is not worn for charging.

Therefore, due to the aforementioned limitations, at present, the electronic device may be provided with inaccurate information or limited information in a situation where continuous information about a long duration, such as life rhythm, activity information, or sleep information, is required, or information that can be provided may be limited.

SUMMARY

The present disclosure has been made to address at least the above-mentioned disadvantages and to provide at least the advantages described below.

Accordingly, an aspect of the present disclosure provides an electronic device including an electrode on a front side, and an operating method thereof.

According to an aspect of the present disclosure, an electronic device is provided that is capable of maintaining continuity of health information by acquiring user's health information even when the electronic device is being charged, and an operating method thereof.

According to an aspect of the present disclosure, an electronic device is provided that is capable of supporting charging even in a state where the electronic device is not detached from a user's body, and an operating method thereof.

According to an aspect of the present disclosure, an electronic device is provided having a front electrode and capable of performing charging based on a wired or wireless charging cradle by using the front electrode, and an operating method thereof.

According to an aspect of the present disclosure, an electronic device is provided that is capable of receiving continuous health information without a limitation based on charging of the electronic device, and an operating method thereof.

In accordance with an aspect of the present disclosure, an electronic device includes a battery, a charging circuit for charging the battery, a bio-sensor, and a processor. The processor may be configured to determine whether the battery is charged through the charging circuit, if the battery is not charged, acquire biometric information by using a first method through the bio-sensor, and if the battery is charged, acquire the biometric information by using a second method through the bio-sensor.

In accordance with an aspect of the present disclosure, a method of operating an electronic device includes determining whether a battery is charged through a charging circuit, if the battery is not charged, acquiring biometric information by using a first method through a bio-sensor, and if the battery is charged, acquiring the biometric information by using a second method through the bio-sensor.

BRIEF DESCRIPTION OF THE DRAWINGS

The above and other aspects, features, and advantages of the present disclosure will be more apparent from the following detailed description when taken in conjunction with the accompanying drawings, in which.

DETAILED DESCRIPTION

Figure 1:
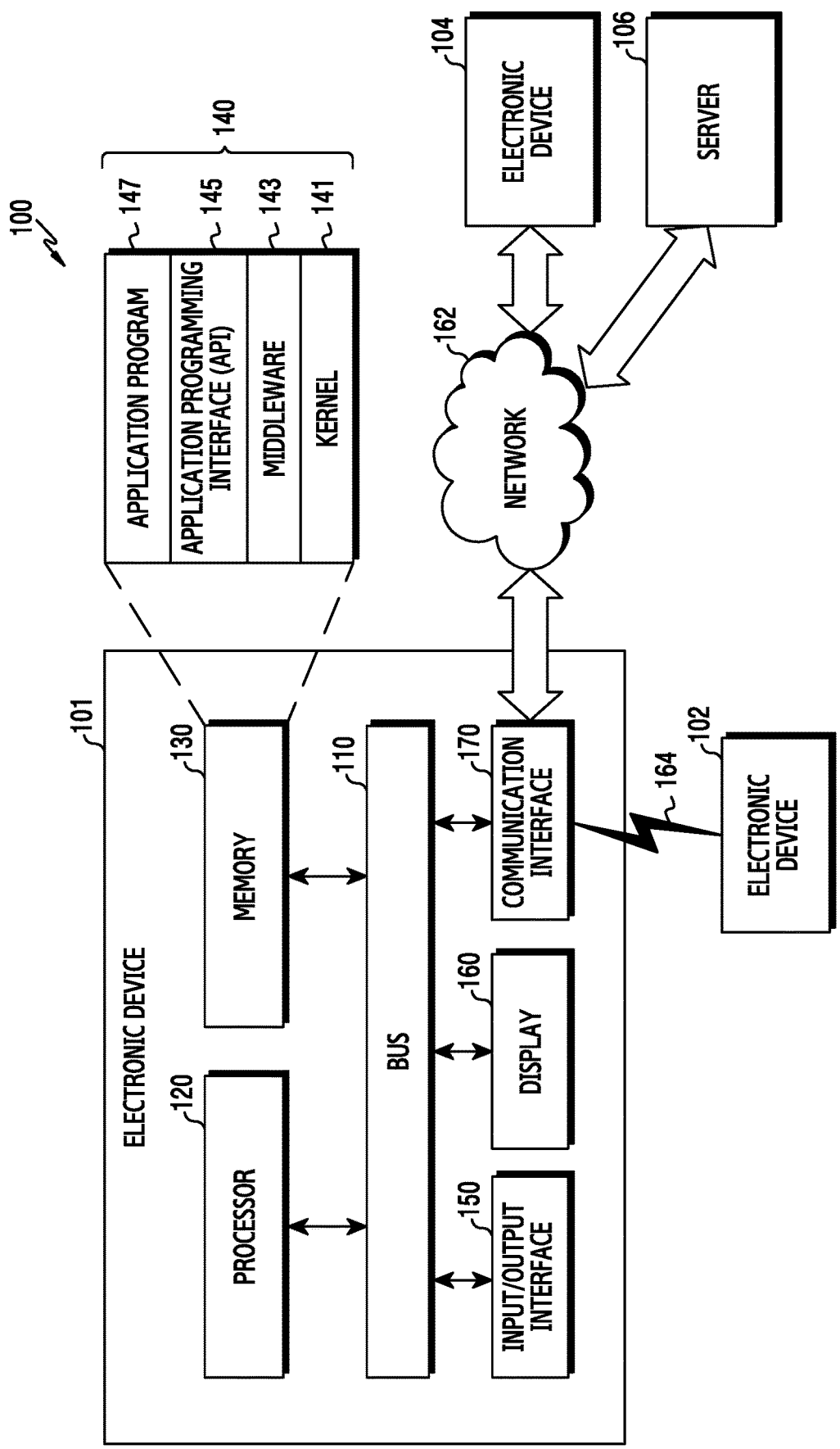
FIG. 1 illustrates a network environment including an electronic device, according to an embodiment of the present disclosure.

Embodiments of the present disclosure will be described with reference to the accompanying drawings. The same or similar components may be designated by the same or similar reference numerals although they are illustrated in different drawings. Detailed descriptions of constructions or processes known in the art may be omitted to avoid obscuring the subject matter of the present disclosure.

As used herein, the terms "have", "may have", "include", or "may include" refers to the existence of a corresponding feature (e.g., numeral, function, operation, or constituent element such as component), and do not exclude one or more additional features.

The expressions "A or B", "at least one of A and/or B", or "one or more of A and/or B" may include all possible combinations of the items listed. For example, the expressions "A or B", "at least one of A and B", or "at least one of A or B" may refer to including at least one A, including at least one B, or including both at least one A and at least one B.

The expressions "a first", "a second", "the first", or "the second" may modify various components regardless of the order and/or importance, but do not limit the corresponding components. For example, a first user device and a second user device indicate different user devices, although both of them are user devices. A first element may be referred to as a second element, and similarly, a second element may be referred to as a first element without departing from the scope of the present disclosure.

When an element (e.g., a first element) is referred to as being operatively or communicatively "connected," or "coupled," to another element (e.g., a second element), it may be directly connected or coupled directly to the other element or any other element (e.g., a third element) may be interposer between them. In contrast, when an element (e.g., a first element) is referred to as being "directly connected," or "directly coupled" to another element (e.g., a second element), there is no element (e.g., a third element) interposed between them.

The expression "configured to", as used in the present disclosure, may be used interchangeably with, "suitable for", "having the capacity to", "designed to", "adapted to", "made to", or "capable of", according to the situation. The expression "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g. an embedded processor) only for performing the corresponding operations or a generic-purpose processor (e.g., a central processing unit (CPU) or application processor (AP)) that can perform the corresponding operations by executing one or more software programs stored in a memory device.

The terms used herein are merely for the purpose of describing particular embodiments and are not intended to limit the scope of the present disclosure. Terms of a singular form may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the same meanings as the contextual meanings in the relevant field of art, and are not to be interpreted to have ideal or excessively formal meanings unless clearly defined in the present disclosure.

An electronic device, according to the present disclosure, may include at least one of a smart phone, a tablet personal computer (PC), a mobile phone, a video phone, an electronic book reader (e-book reader), a desktop PC, a laptop PC, a netbook computer, a workstation, a server, a personal digital assistant (PDA), a portable multimedia player (PMP), an MPEG-1 audio layer-3 (MP3) player, a mobile medical device, a camera, and a wearable device. The wearable device may include at least one of an accessory type (e.g., a watch, a ring, a bracelet, an anklet, a necklace, glasses, a contact lens, or a head-mounted device (HMD)), a fabric or clothing integrated type (e.g., electronic clothing), a body-mounted type device (e.g., a skin pad or tattoo), and a bio-implantable type device (e.g., an implantable circuit).

According to some embodiments of the present disclosure, the electronic device may be a home appliance. The home appliance may include at least one of a television, a digital video disk (DVD) player, an audio device, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

The electronic device may include at least one of various medical devices (e.g., various portable medical measuring devices (blood glucose monitoring devices, heart rate monitoring devices, blood pressure measuring devices, or body temperature measuring devices), a magnetic resonance angiography (MRA), a magnetic resonance imaging (MRI), a computed tomography (CT) machine, and an ultrasonic machine), a navigation device, a global positioning system (GPS) receiver, an event data recorder (EDR), a flight data recorder (FDR), vehicle infotainment devices, an electronic device for a ship (e.g., a navigation device for a ship and a gyro-compass), avionics, security devices, an automotive head unit, a robot for home or industry, an automatic teller machine (ATM), point of sales (POS) devices in a shop, or an Internet of things (IoT) device (e.g., a light bulb, various sensors, an electric or gas meter, a sprinkler device, a fire alarm, a thermostat, a streetlamp, a toaster, a sporting goods device, a hot water tank, a heater, or a boiler).

The electronic device may include at least one of a part of furniture or a building/structure, an electronic board, an electronic signature receiving device, a projector, and various types of measuring instruments (e.g., water meters, electric meters, gas meters, and radio wave meters). The electronic device may be a combination of one or more of the aforementioned various devices. The electronic device may be a flexible device. Further, the electronic device is not limited to the aforementioned devices, and may include a new electronic device according to the development of new technologies.

Hereinafter, the term "user" may indicate a person who uses an electronic device or a device (e.g., an artificial intelligence electronic device) that uses an electronic device.

FIG. 1 illustrates a network environment including an electronic device, according to an embodiment of the present disclosure.

Referring to FIG. 1, an electronic device 101 includes a bus 110, a processor 120, a memory 130, an input/output interface 150, a display 160, and a communication interface 170. The electronic device 101 may omit at least one of the above elements or may further include other elements.

The bus 110 may include a circuit for connecting the elements 110-170 and transferring control messages and/or data between the elements.

The processor 120 may include one or more of a CPU, an AP, and a communication processor (CP). The processor 120 may carry out operations or data processing relating to control and/or communication of at least one other element of the electronic device 101.

The memory 130 may include a volatile memory and/or a non-volatile memory. The memory 130 may store instructions or data relevant to at least one other element of the electronic device 101. The memory 130 may store software and/or a program 140. The program 140 may include a kernel 141, middleware 143, an application programming interface (API) 145, and/or an application program (or "applications") 147. At least some of the kernel 141, the middleware 143, and the API 145 may be referred to as an operating system (OS).

The memory 130 may store one or more programs executed by the processor 120, and may perform a function for temporarily storing data to be input/output. The data to be input/output may include a file such as biometric information, health information, charging data, a video, an image (e.g., a photo), or audio data. The memory 130 may play a role of storing acquired data. Data acquired on a real-time basis is stored in a temporary storage device (e.g., a buffer) and data confirmed to be stored is stored in a long-term storage device. The memory 130 may include a computer readable recording medium having a program recorded thereon to execute the method in the processor 120.

The kernel 141 may control or manage system resources (e.g., the bus 110, the processor 120, or the memory 130) used for performing an operation or function implemented by the other programs (e.g., the middleware 143, the API 145, or the application program 147). Furthermore, the kernel 141 may provide an interface through which the middleware 143, the API 145, or the application program 147 may access the individual elements of the electronic device 101 to control or manage the system resources.

The middleware 143 may function as an intermediary for allowing the API 145 or the application program 147 to communicate with the kernel 141 to exchange data.

In addition, the middleware 143 may process one or more operation requests received from the application program 147 according to priority. For example, the middleware 143 may give priority to use the system resources (e.g., the bus 110, the processor 120, and the memory 130) of the electronic device 101, to at least the application program 147. For example, the middleware 143 may perform scheduling or load balancing with respect to the one or more operation requests by processing the one or more operation requests according to the priority given to the at least one application program.

The API 145 is an interface through which the application program 147 controls functions provided from the kernel 141 or the middleware 143, and may include at least one interface or function (e.g., instruction) for file control, window control, image processing, or text control.

The input/output interface 150 may function as an interface that transfers instructions or data input from a user or another external device to the other element(s) of the electronic device 101. Furthermore, the input/output interface 150 may output the instructions or data received from the other element(s) of the electronic device 101 to the user or another external device.

The display 160 may include a liquid crystal display (LCD), a light emitting diode (LED) display, an organic light emitting diode (OLED) display, a micro electro mechanical system (MEMS) display, or an electronic paper display. The display 160 may display various types of content (e.g., text, images, videos, icons, or symbols) for the user. The display 160 may include a touch screen and receive a touch, a gesture, a proximity or hovering input, using an electronic pen or the user's body part.

The display 160 may show a visual output to the user. The visual output may be shown as a text, a graphic, a video, or a combination thereof. The display 160 may display (output) a variety of information processed in the electronic device 101. The display 160 may display a user interface (UI) or a graphic UI (GUI) related to a usage of the electronic device or related to an operation (e.g., an operation of measuring biometric information, an operation of providing health information, or an operation of providing a charging state) performed by the electronic device 101.

The communication interface 170 may set communication between the electronic device 101 and an external device (e.g., the first external electronic device 102, the second external electronic device 104, or a server 106). The communication interface 170 may be connected to a network 162 through wireless or wired communication to communicate with the external device (e.g., the second external electronic device 104 or the server 106).

The wireless communication may use at least one of long term evolution (LTE), LTE-advance (LTE-A), code division multiple access (CDMA), wideband CDMA (WCDMA), universal mobile telecommunications system (UMTS), wireless broadband (WiBro), and global system for mobile communications (GSM), as a cellular communication protocol. In addition, the wireless communication may include short range communication 164 performed by using at least one of Wi-Fi, bluetooth, bluetooth low energy (BLE), near field communication (NFC), and global navigation satellite system (GNSS). The GNSS may include at least one of a global positioning System (GPS), a global navigation satellite system (Glonass), a Beidou navigation satellite system (Beidou), and a European global satellite-based navigation system (Galileo), according to a use area, or a bandwidth. Hereinafter, "GPS" may be interchangeably used with the "GNSS". The wired communication may include at least one of a universal serial bus (USB), a high definition multimedia interface (HDMI), recommended standard 232 (RS-232), and a plain old telephone service (POTS). The network 162 may include at least one of a communication network such as a computer network (e.g., a LAN or a WAN), the Internet, and a telephone network.

Each of the first and second external electronic apparatuses 102 and 104 may be of a type identical to or different from that of the electronic apparatus 101. The server 106 may include a group of one or more servers. All or some of the operations performed in the electronic device 101 may be performed in another electronic device or a plurality of the electronic devices 102 and 104 or the server 106. When the electronic device 101 has to perform some functions or services automatically or in response to a request, the electronic device 101 may make a request for performing at least some functions relating thereto to the electronic device 102 or 104 or the server 106, instead of, or in addition to, performing the functions or services by itself. Another electronic apparatus may execute the requested functions or the additional functions, and may deliver a result of the execution to the electronic apparatus 101. The electronic device 101 may process the received result as it is or additionally to provide the requested functions or services. Cloud computing, distributed computing, or client-server computing technology may be used to achieve this.

Figure 2:
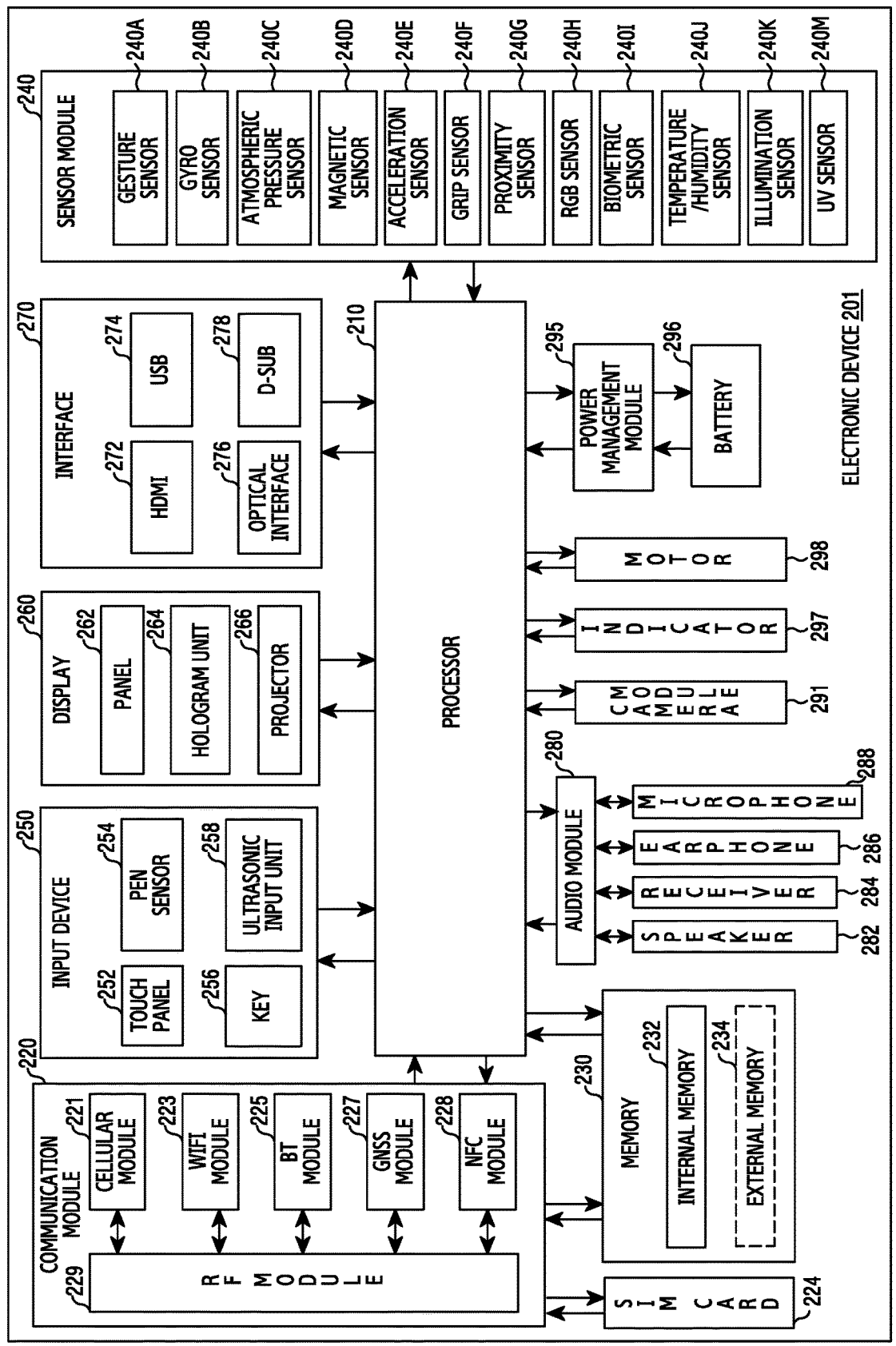
FIG. 2 is a block diagram of an electronic device, according to an embodiment of the present disclosure.

FIG. 2 is a block diagram illustrating an electronic device, according to an embodiment of the present disclosure.

Referring to FIG. 2, the electronic apparatus 201 may include the whole or part of the electronic apparatus 101 illustrated in FIG. 1. The electronic device 201 includes at least one AP 210, a communication module 220, a subscriber identification module (SIM) 224, a memory 230, a sensor module 240, an input device 250, a display 260, an interface 270, an audio module 280, a camera module 291, a power management module 295, a battery 296, an indicator 297, and a motor 298.

The AP 210 may control a plurality of hardware or software components connected to the AP 210 by driving an operating system or an application program and perform processing of various pieces of data and calculations. The AP 210 may be implemented by a system on chip (SoC). The AP 210 may further include a graphic processing unit (GPU) and/or an image signal processor. The AP 210 may include at least some (e.g., a cellular module 221) of the elements illustrated in FIG. 2. The AP 210 may load, into a volatile memory, instructions or data received from at least one (e.g., a non-volatile memory) of the other elements and may process the loaded instructions or data, and may store various data in a non-volatile memory.

The communication module 220 may have a configuration equal or similar to that of the communication interface 170 of FIG. 1. The communication module 220 may include the cellular module 221, a Wi-Fi module 223, a bluetooth (BT) module 225, a GNSS module 227 (e.g., a GPS module, a Glonass module, a Beidou module, or a Galileo module), a near field communication (NFC) module 228, and a radio frequency (RF) module 229.

The cellular module 221 may provide a voice call, image call, a text message service, or an Internet service through a communication network. The cellular module 221 may distinguish between and authenticate electronic devices 201 within a communication network using the SIM card 224. The cellular module 221 may perform at least some of the functions that the AP 210 may provide. The cellular module 221 may include a CP.

Each of the Wi-Fi module 223, the BT module 225, the GNSS module 227, and the NFC module 228 may include a processor for processing data transmitted and received through the relevant module. At least some (e.g., two or more) of the cellular module 221, the Wi-Fi module 223, the BT module 225, the GNSS module 227, and the NFC module 228 may be included in one integrated chip (IC) or IC package.

At least one of the cellular module 221, the Wi-Fi module 223, the BT module 225, the GNSS module 227, and the NFC module 228 may transmit and receive RF signals through a separate RF module.

The SIM 224 may include a card including a subscriber identity module and/or an embedded SIM, and may contain unique identification information (e.g., an integrated circuit card identifier (ICCID)) or subscriber information (e.g., an international mobile subscriber identity (IMSI)).

The memory 230 includes an embedded memory 232 or an external memory 234. The embedded memory 232 may include at least one of a volatile memory (e.g., a dynamic random access memory (DRAM), a static RAM (SRAM), and a synchronous dynamic RAM (SDRAM)) and a non-volatile memory (e.g., a one time programmable read only memory (OTPROM), a programmable ROM (PROM), an erasable and programmable ROM (EPROM), an electrically erasable and programmable ROM (EEPROM), a mask ROM, a flash ROM, a flash memory (e.g., a NAND flash memory or a NOR flash memory), a hard disc drive, and a solid state drive (SSD)).

The application module may include an application for providing health care information (e.g., a measurement on a physical activity level or a blood sugar level), or environment information (e.g., atmospheric pressure, humidity, or temperature information). The application module may include one or more processing modules to allow the electronic device 201 to switch to a mode based on a normal usage mode, a charging mode, or a simultaneous mode for measuring and charging, or to perform a related operation in a corresponding mode.

The external memory 234 may further include a flash drive, such as, a compact flash (CF), a secure digital (SD) memory, a micro secure digital (Micro-SD) memory, a mini secure digital (Mini-SD) memory, an eXtreme digital (xD) memory, or a memory stick. The external memory 234 may be functionally and/or physically connected to the electronic apparatus 201 through various interfaces.

The sensor module 240 may measure a physical quantity or detect an operation state of the electronic device 201, and may convert the measured or detected information into an electrical signal. The sensor module 240 includes at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., a red green blue (RGB) sensor), a bio-sensor 240I, a temperature/humidity sensor 240J, a light sensor 240K, and an ultra violet (UV) sensor 240M. Additionally or alternatively, the sensor module 240 may include an E-nose sensor, an electromyography (EMG) sensor, an electroencephalogram (EEG) sensor, an electrocardiogram (ECG) sensor, an infrared (IR) sensor, an iris sensor, and/or a fingerprint sensor. The sensor module 240 may further include a control circuit for controlling one or more sensors included therein. The electronic apparatus 201 may further include a processor configured to control the sensor module 240 as a part of or separately from the AP 210, and may control the sensor module 240 while the AP 210 is in a sleep state.

The input device 250 includes a touch panel 252, a digital pen sensor 254, a key 256, or an ultrasonic input device 258. The touch panel 252 may use at least one of a capacitive type, a resistive type, an infrared type, and an ultrasonic type touch panel. Also, the touch panel 252 may further include a control circuit and a tactile layer to provide a tactile reaction to the user.

The digital pen sensor 254 may include a recognition sheet which is a part of the touch panel or is separated from the touch panel. The key 256 may include a physical button, an optical key or a keypad. The ultrasonic input device 258 may detect ultrasonic wavers generated by an input tool through a microphone 288 and identify data corresponding to the detected ultrasonic waves.

The display 260 includes a panel 262, a hologram device 264 or a projector 266. The panel 262 may include a configuration that is identical or similar to the display 160 illustrated in FIG. 1. The panel 262 may be implemented to be flexible, transparent, or wearable. The panel 262 and the touch panel 252 may be implemented as one module. The hologram 264 may show a three dimensional image in the air by using an interference of light. The projector 266 may display an image by projecting light onto a screen. The screen may be located inside or outside the electronic apparatus 201. According to an embodiment, the display 260 may further include a control circuit for controlling the panel 262, the hologram device 264, or the projector 266.

The interface 270 includes an HDMI 272, a USB 274, an optical interface 276, or a D-subminiature (D-sub) 278. The interface 270 may be included in the communication interface 170 illustrated in FIG. 1. Additionally or alternatively, the interface 270 may include a mobile high-definition link (MHL) interface, an SD card/multi-media card (MMC) interface, or an Infrared Data Association (IrDA) standard interface.

The audio module 280 may bilaterally convert a sound and an electrical signal. At least some elements of the audio module 280 may be included in the input/output interface 145 illustrated in FIG. 1. The audio module 280 may process sound information which is input or output through a speaker 282, a receiver 284, earphones 286, or the microphone 288.

The camera module 291 is a device which may photograph a still image and a dynamic image. The camera module 291 may include one or more image sensors (e.g., a front sensor or a back sensor), a lens, an image signal processor (ISP) or a flash (e.g., a LED or xenon lamp).

The power management module 295 may manage power of the electronic device 201. The power management module 295 includes a power management integrated circuit (PMIC), a charger integrated circuit (IC), or a battery gauge. The PMIC may use a wired and/or wireless charging method. The wireless charging method may include a magnetic resonance method, a magnetic induction method, and an electromagnetic method. Additional circuits (e.g., a coil loop, a resonance circuit, and a rectifier) for wireless charging may be further included. The battery gauge may measure a residual quantity of the battery 296, and a voltage, a current, or a temperature. The battery 296 may include a rechargeable battery or a solar battery.

The indicator 297 may display a particular state (e.g., a booting state, a message state, or a charging state) of the electronic apparatus 201 or a part (e.g., the AP 210). The motor 298 may convert an electrical signal into mechanical vibration, and may generate a vibration or a haptic effect. The electronic apparatus 201 may include a processing unit (e.g., a GPU) for supporting a mobile television (TV). The processing unit for supporting mobile TV may process media data according to a certain standard such as digital multimedia broadcasting (DMB), digital video broadcasting (DVB), or mediaFLO™.

Each of the above-described component elements of hardware may be configured with one or more components, and the names of the corresponding component elements may vary based on the type of electronic device. The electronic device may include at least one of the aforementioned elements. Some elements may be omitted or other additional elements may be further included in the electronic device. Also, some of the hardware components according to various embodiments may be combined into one entity, which may perform functions identical to those of the relevant components before the combination.

Figure 3:
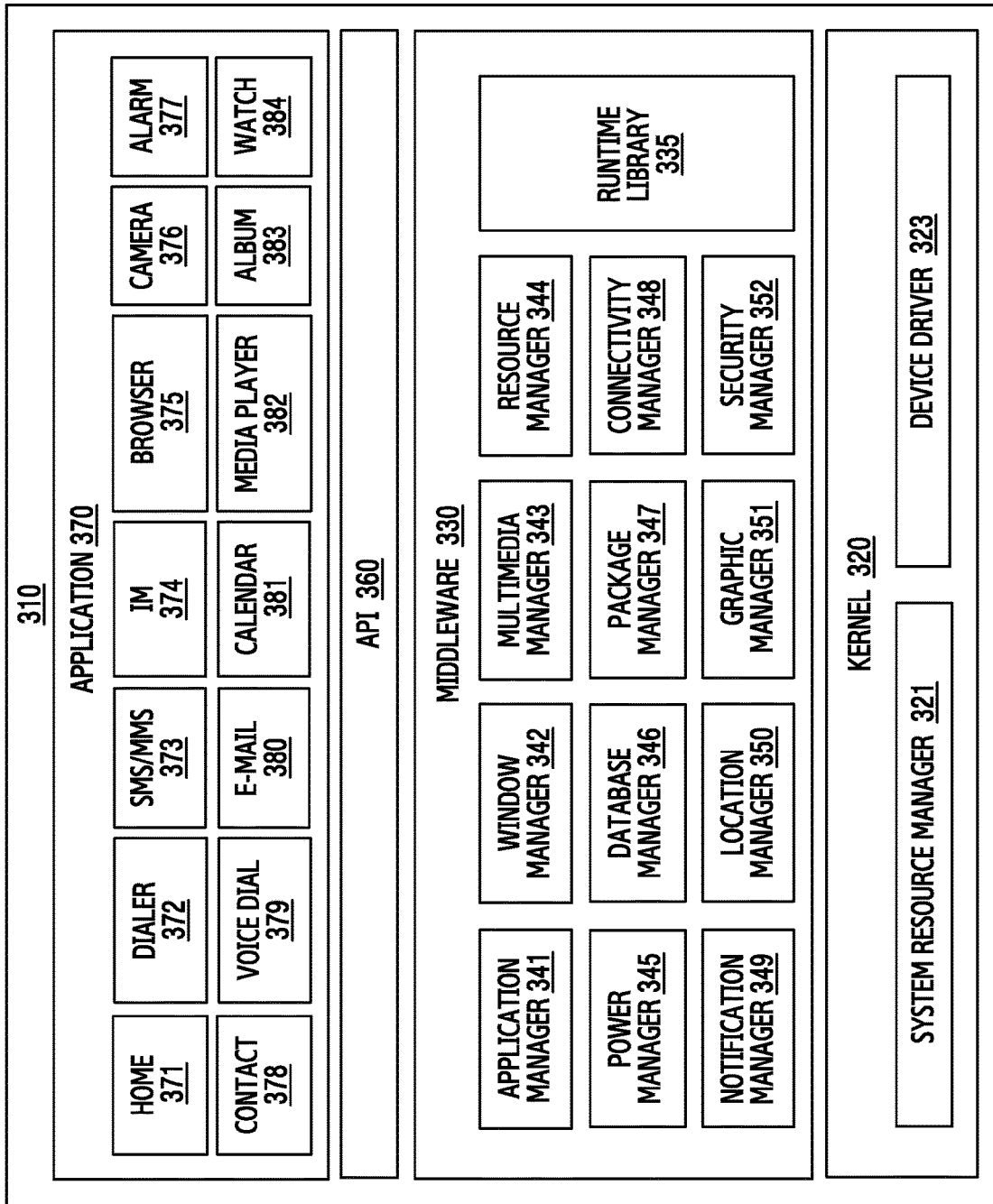
FIG. 3 is a block diagram of a program module, according to an embodiment of the present disclosure.

FIG. 3 is a block diagram of a program module, according to an embodiment of the present disclosure.

Referring to FIG. 3, the program module 310 may include an OS for controlling resources related to the electronic device electronic device 101 and/or various applications (e.g., the application program 147) executed in the OS. The OS may be Android™, iOS™, Windows™, Symbian™, Tizen™, or Bada™.

The program module 310 includes a kernel 320, middleware 330, an API 360, and/or an application 370. At least some of the program module 310 may be preloaded on the electronic apparatus, or may be downloaded from the electronic apparatus 102 or 104, or the server 106.

The kernel 320 includes a system resource manager 321 and/or a device driver 323. The system resource manager 321 may perform the control, allocation, or retrieval, of system resources. The system resource manager 321 may include a process manager, a memory manager, or a file system manager. The device driver 323 may include a display driver, a camera driver, a bluetooth driver, a shared memory driver, a USB driver, a keypad driver, a Wi-Fi driver, an audio driver, or an inter-process communication (IPC) driver.

The middleware 330 may provide a function required by the applications 370 in common or provide various functions to the applications 370 through the API 360 so that the applications 370 can efficiently use limited system resources within the electronic device. The middleware 330 includes at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module that a compiler uses in order to add a new function through a programming language while the applications 370 are being executed. The runtime library 335 may perform input/output management, memory management, or the functionality for an arithmetic function.

The application manager 341 may manage the life cycle of at least one of the applications 370. The window manager 342 may manage GUI resources used for the screen. The multimedia manager 343 may determine a format required to reproduce various media files, and may encode or decode a media file by using a coder/decoder (codec) appropriate for the relevant format. The resource manager 344 may manage resources, such as a source code, a memory, and a storage space, of at least a part of the application 370.

The power manager 345 may operate together with a basic input/output system (BIOS) to manage a battery or power and may provide power information required for the operation of the electronic device. The database manager 346 may generate, search for, and/or change a database to be used by at least one of the applications 370. The package manager 347 may manage the installation or update of an application distributed in the form of a package file.

The connectivity manager 348 may manage a wireless connection such as Wi-Fi or bluetooth. The notification manager 349 may display or notify of an event, such as an arrival message, an appointment, and a proximity notification, so as not to disturb the user. The location manager 350 may manage location information of the electronic apparatus. The graphic manager 351 may manage a graphic effect, which is to be provided to the user, or a user interface related to the graphic effect. The security manager 352 may provide various security functions required for system security and user authentication. When the electronic apparatus 101 has a telephone call function, the middleware 330 may further include a telephony manager for managing a voice call function or a video call function of the electronic apparatus.

The middleware 330 may include a middleware module that forms a combination of various functions of the above-described elements. The middleware 330 may provide a module specialized for each type of OS in order to provide a differentiated function. Also, the middleware 330 may dynamically delete some of the existing elements, or may add new elements.

The API 360 is a set of API programming functions, and may be provided with a different configuration according to an OS. For example, in the case of Android™ or iOS™, one API set may be provided for each platform. In the case of Tizen™, two or more API sets may be provided for each platform.

The application 370 may include one or more applications which can provide functions such as a home application 371, a dialer application 372, an SMS/MMS application 373, an instant message (IM) application 374, a browser application 375, a camera application 376, an alarm application 377, a contacts application 378, a voice dialer application 379, an email application 380, a calendar application 381, a media player application 382, an album application 383, a clock application 384, a health care application (e.g., an application for measuring exercise quantity or blood sugar), or an environment information application (e.g., an application for gathering atmospheric pressure, humidity, or temperature information).

The application 370 may include an information exchange application that supports information exchange between the electronic apparatus 101 and an external electronic apparatus (e.g., the electronic apparatus 102 or 104). The information exchange application may include a notification relay application for forwarding specific information to an external electronic device, or a device management application for managing an external electronic device.

The notification relay application may include a function of delivering, to the external electronic apparatus, notification information generated by other applications (e.g., an SMS/MMS application, an email application, a health care application, or an environmental information application) of the electronic apparatus 101. Further, the notification relay application may receive notification information from an external electronic device and provide the received notification information to a user.

The device management application may manage (e.g., install, delete, or update) a function for at least a part of the external electronic device communicating with the electronic device (e.g., turning on/off the external electronic device itself (or some elements thereof) or adjusting brightness (or resolution) of a display), applications executed in the external electronic device, or services provided from the external electronic device (e.g., a telephone call service or a message service).

The application 370 may include applications (e.g., a health care application of a mobile medical appliance) designated according to attributes of the external electronic device 102 or 104. The application 370 may include an application received from the external electronic apparatus. The application 370 may include a preloaded application or a third party application which can be downloaded from the server. Names of the elements of the program module 310, according to the above-described embodiments of the present disclosure, may change depending on the type of OS.

At least a part of the program module 310 may be implemented in software, firmware, hardware, or a combination thereof. At least a part of the program module 310 may be implemented (e.g., executed) by the AP 210. At least a part of the program module 310 may include a module, a program, a routine, a set of instructions, and/or a process for performing one or more functions.

The term "module" as used herein may mean a unit including one of hardware, software, and firmware or a combination of two or more of them. The "module" may be interchangeably used with the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" may include at least one of an application-specific integrated circuit (ASIC) chip, a field-programmable gate arrays (FPGA), and a programmable-logic device for performing operations which has been known or are to be developed hereinafter.

According to an embodiment of the present disclosure, the module or the program module may include one or more elements described above; exclude some of them; or further include other elements. The operations performed by the module, the program module, or other elements may be executed in a sequential, parallel, iterative, or heuristic method. In addition, some operations may be executed in a different order, or may be omitted, or other operations may be added. Therefore, the scope of various embodiments of the present document should be construed to encompass all modifications or various other embodiments based on the technical concept of the various embodiments of the present disclosure.

Figure 4:
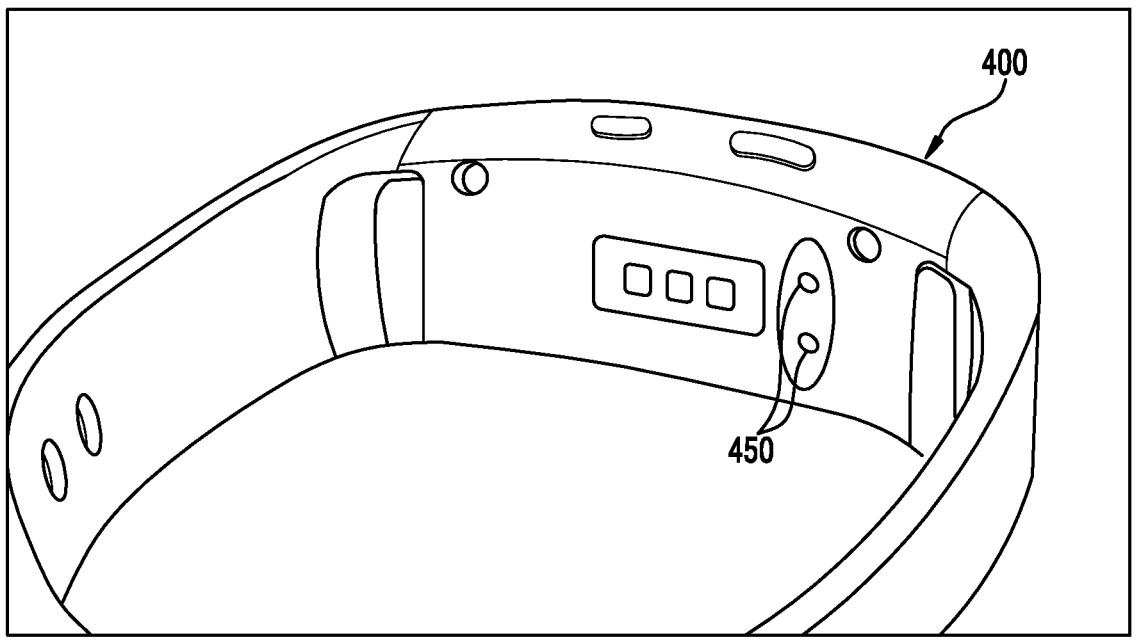
FIG. 4, FIG. 5, and FIG. 6 illustrate an electronic device, according to an embodiment of the present disclosure.
Figure 5:
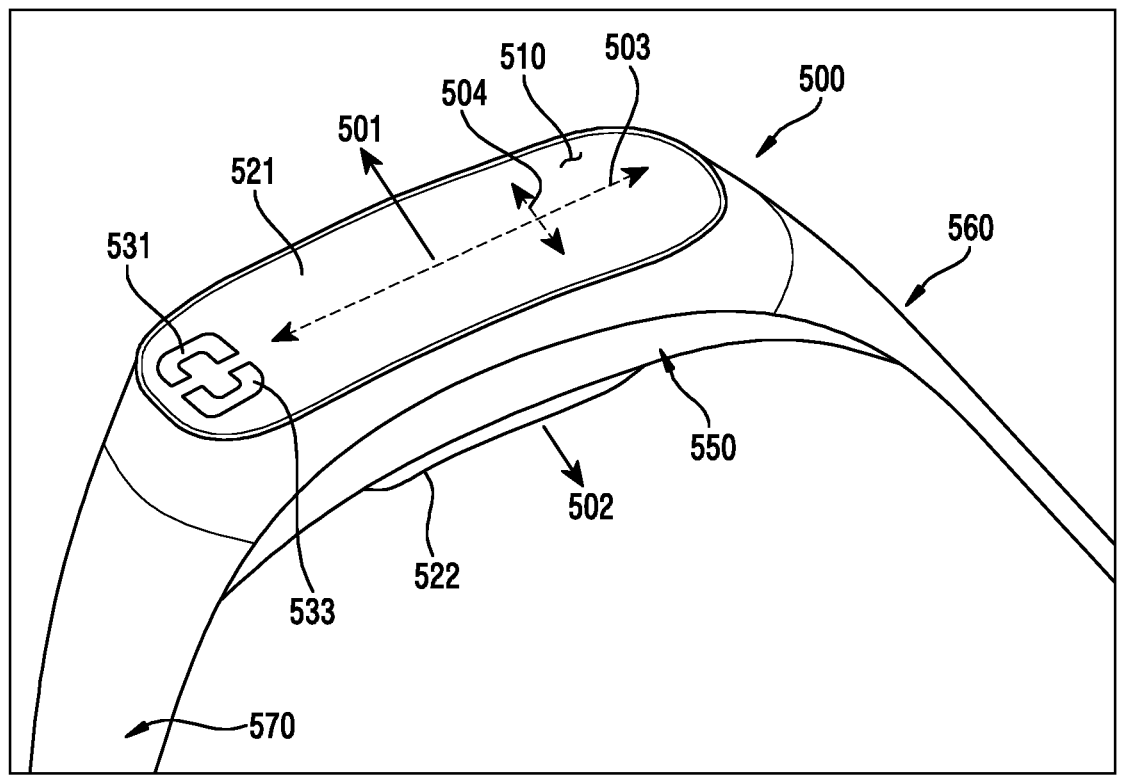
Figure 6:
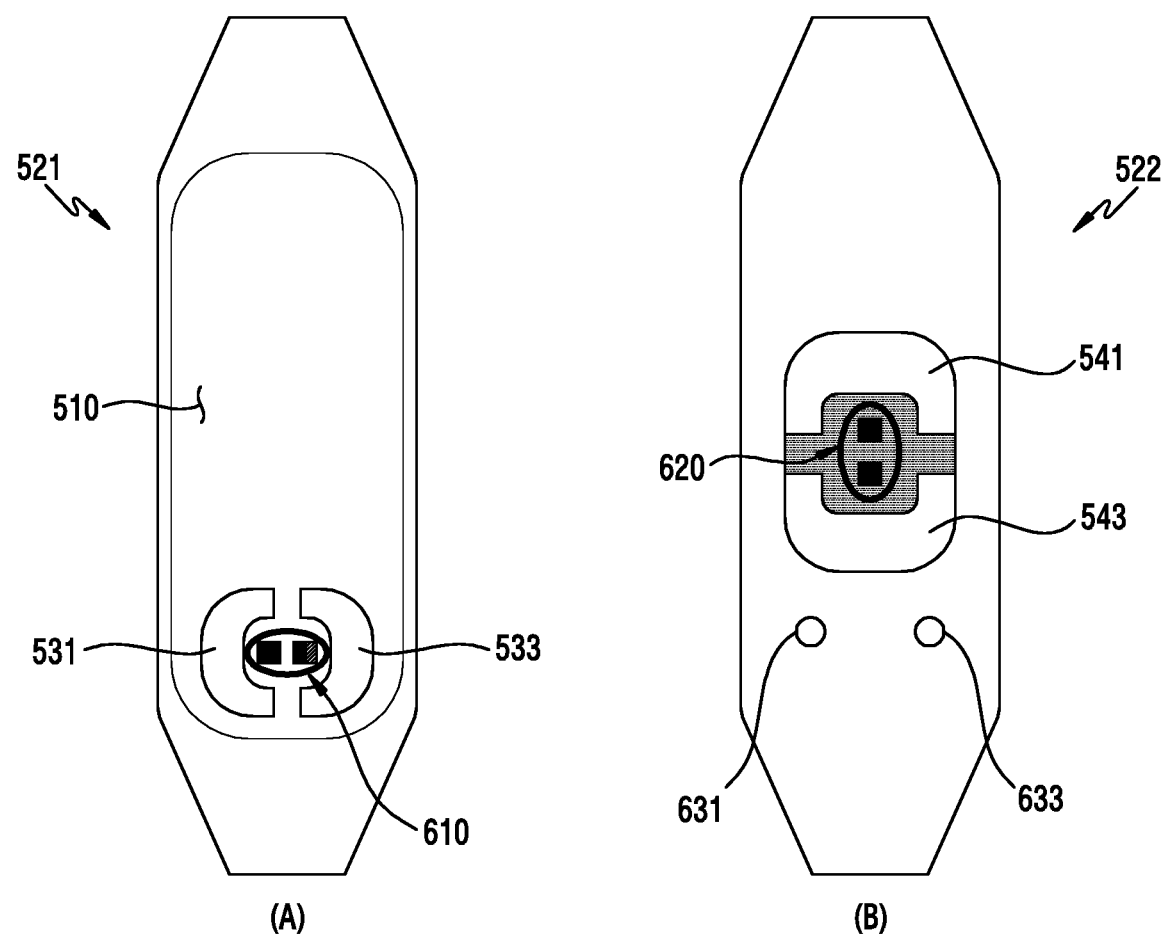

FIG. 4, FIG. 5, and FIG. 6 illustrate an electronic device, according to various embodiments of the present disclosure.

An external structure of a normal electronic device 400 (e.g., a wrist wearable device) is illustrated in FIG. 4, and an electronic device 500 (e.g., a wrist wearable device) is illustrated in FIG. 5.

Referring to FIG. 4, the normal electronic device 400 may include two additional electrodes 450 or charging electrodes (or charging ports) on a rear or lateral side of the electronic device 400 to charge the electronic device 400. The two electrodes 450 of the electronic device 400 may be used to measure biometric information.

In a case of the normal electronic device 400, user's biometric information cannot be measured during charging because the electronic device 400 must be separated from a user's body (e.g., wrist) for charging. Since the normal electronic device 400 must be separated from the wrist for charging, user's health information cannot be acquired during a charging time, which results in a problem in that continuity of the health information cannot be maintained. In addition, the normal electronic device 400 has a problem in that the accuracy of the health information based on the biometric information deteriorates because a period of acquiring the health information must be set for a long time in order to maximize a usage time after the electronic device is fully charged. Due to such a problem, the normal electronic device 400 may be provided with inaccurate information or limited information in a situation where continuous information regarding a long duration such as life rhythm, activity information or sleep information is required, or information that can be provided may be limited.

In various exemplary embodiments of the present disclosure, charging may be possible even if the electronic device 500 is not detached for charging. The user's biometric information may be continuously acquired even while the electronic device 500 is being charged, thereby maintaining continuity of the health information, as shown in FIG. 5.

Referring to FIG. 5, the electronic device 500 includes an electrode 531, 533 (e.g., a first electrode 531 (e.g., a positive (+) electrode) and a second electrode 533 (e.g., a negative (−) electrode)) (hereinafter, a front electrode 531, 533) on a front side (e.g., a side on which a display 510 is disposed) of the electronic device 500. The electronic device 500 may provide charging using a wired or wireless cradle by using the front electrode 531, 533. In addition, the electronic device 500 may measure and provide biometric information using the front electrode 531, 533. The electronic device 500 may use the front electrode 531, 533 to acquire a user's biometric information without interruption even during charging, thereby providing continuous health information.

As shown in FIG. 5, the electronic device 500 may include a watch configured to include a body 550 including the display 510, a first extension 560, and a second extension 570 (e.g., a band or a strap) extended at both sides of the body 550.

The body 550 includes a first side 521 (e.g., a front side) facing a first direction 501 and a second side 522 (e.g., a rear side) facing a second direction 502 opposite to the first direction 501.

The display 510 may be disposed between the first side 521 and the second side 522, and exposed through the first side 521. When the electronic device 500 is worn on a user's wrist, the second side 522 may be in contact with the user's wrist.

The electronic device 500 includes at least one front electrode 531, 533 (e.g., a light-transmitting and conductive region (or conductive electrode)) which forms at least one part of the first surface 521. The at least one front surface 531, 533 may be superposed on any one region of the display 510. The front electrode 531, 533 may be superimposed on a plurality of regions of the display 510. For example, the front electrode 531, 533 may be configured as one pair of the first electrode 531 and the second electrode 533, and may be implemented such that a plurality of front electrodes are superposed on a plurality of regions of the display 510.

The at least one front electrode 531, 533 may be configured such that at least one part thereof is included in a first front electrode and a second front electrode disposed in a direction 503 between the extensions 560 and 570 and a third front electrode and a fourth front electrode disposed in a direction 504 orthogonal to the direction 503. The electronic device 500 may operate by selecting at least one of a plurality of front electrodes of the first side 510 on the basis of a biometric measurement mode selected by the user. The electronic device 500 may include at least one electrode (e.g., a rear electrode) which forms at least one part of the second side 522.

An example of the structure of a front side along the first side 521 of the electronic device 500 and a rear side along the second side 522 is illustrated in FIG. 6.

The first side 521 (the front side) of the electronic device 500 may include, as shown in FIG. 6, the display 510, the front electrode 531, 533 (e.g., the first electrode 531 (e.g., a positive (+) electrode) and the second electrode 533 (e.g., a negative (−) electrode)), and a front optic sensor 610. The second side 522 (e.g., the rear portion) of the electronic device 500 may include, as shown in item B of FIG. 6, a rear electrode 541, 543 (e.g., a third electrode 541 (e.g., a positive (+) electrode) and a fourth electrode 543 (e.g., a negative (−) electrode)), a rear optic sensor 620, and a charging electrode (e.g., a first charging electrode 631 and a second charging electrode 633). The structure and operation of the constitutional elements illustrated in FIG. 5 and FIG. 6 will be described in detail with reference to FIG. 7.

Figure 7:
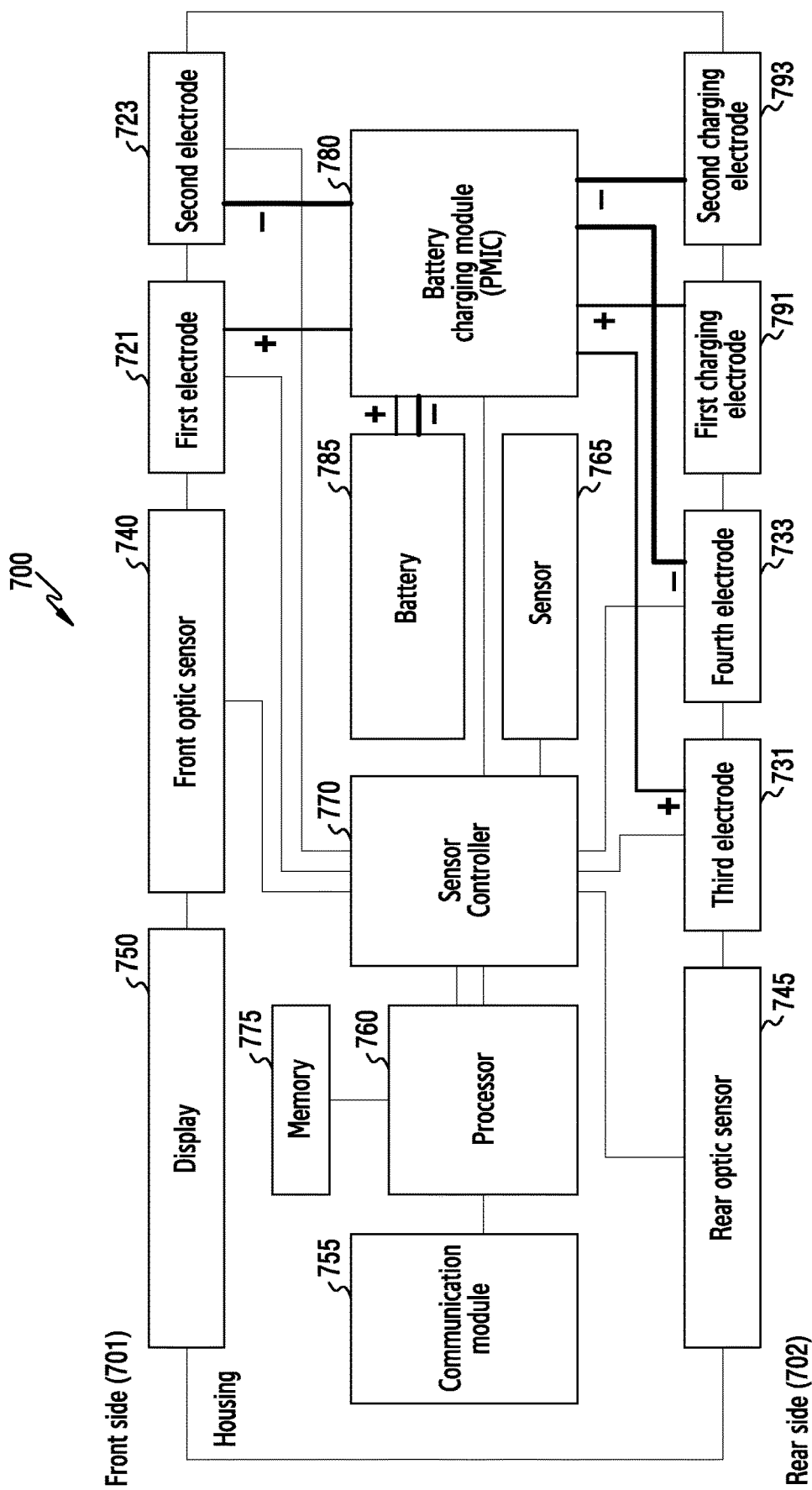
FIG. 7 illustrates a structure of an electronic device, according to an embodiment of the present disclosure.

FIG. 7 illustrates a structure of an electronic device, according to an embodiment of the present disclosure.

Referring to FIG. 7, an electronic device 700 includes a housing, electrodes 721, 723, 731, and 733, optic sensors 740 and 745, a display 750, a communication module 755, a processor 760, a sensor 765, a sensor controller 770, a memory 775, a battery charging module (PMIC) (or a charging circuit) 780, a battery 785, and a charging electrode 791, 793. The electronic device 700 may include constitutional elements corresponding to the front side 701 and the rear side 702. Each constitutional element may be located inside the housing. The display 750, the optic sensors 740 and 745, the various electrodes 721, 723, 731, 733, and 791, 793 may be exposed to the outside.

The housing may represent a body of the electronic device 700. The display 750, the electrodes 721, 723, 731, 733, and 791, 793, and the optic sensors 740 and 745 may be connected to the housing. If the electronic device 700 is an electronic device to be worn on a user's wrist, a connection portion (e.g., the extensions 560 and 570 of FIG. 5) may be connected to the housing. Metal (e.g., steel and aluminum) may be used as a material of the connection portion.

Glass may be disposed to the front side 701. The electronic device 700 may include at least one part of a physical key or touch key on the front side 701 or a lateral side. The electronic device 700 may have a groove (or a notch) for mounting a charging means of the electronic device 700 at both lateral sides of the housing. An additional device (e.g., a charging cradle) may be fixed to the front side 701 of the electronic device 700 by using the grooves at both sides.

The electrodes 721, 723 and 731, 733 are ports (or interfaces) formed of a conductive material, and electric current may flow through the electrodes 721, 723 and 731, 733. The electrodes 721, 723 and 731, 733 may be directly in contact with a user's skin (body) such as a user's finger or hand, or may be indirectly in contact with the user's skin in such a manner that the electrodes are spaced apart by more than a specific distance in a hovering manner while being surrounded by a material such as glass. The electronic device 700 may allow an electric charge to directly flow to a human body through the electrodes 721, 723 and 731, 733, or may measure an output value by using a capacitance value based on the human body and the electric charge.

The electrodes 721, 723 and 731, 733 may include four electrodes in total. The electrodes 721, 723 and 731, 733 may have two electrodes (e.g., a first electrode 721 and a second electrode 723) disposed to the front side 701 of the housing and two electrodes (e.g., a third electrode 731 and a fourth electrode 733) disposed to the rear side 702 of the housing. The two electrodes (e.g., the first electrode 721 and the second electrode 723) located in the front side 701 may be disposed adjacent to each other so that the user can touch the two electrodes 721 and 723 by using one finger.

The electrodes 721, 723 and 731, 733 are measured by using electricity, which may enable a health-related measurement. The electrodes 721, 723 and 731, 733 of the electronic device 700 (e.g., a write-type health wearable device) may be used in an electrocardiography (ECG) measurement for obtaining heartbeat information, a bioelectrical impedance analysis (BIA) measurement for obtaining body fat information, or a galvanic skin response (GSR) measurement for obtaining stress information.

As an electrocardiogram test, the ECG may be a test for measuring an electric potential associated with a heartbeat on a body surface. The electronic device 700 may measure the ECG by selectively using at least three electrodes among the four electrodes 721, 723, 731, and 733 located in the front side 701 and the rear side 702. For example, the ECG may be measured by using the first electrode 721 and the second electrode 723 located in the front side 701 of the electronic device 700 and the third electrode 731 located in the rear side 702 of the electronic device 700.

The BIA may be a test for obtaining body fat information by measuring a resistance between respective electrodes after allowing minute electric current to flow inside the human body. The electronic device 700 may measure the BIA by using all of the electrodes 721 and 723 in the front side 701 and the electrodes 731 and 733 in the rear side 702. For example, the BIA may be measured in such a manner that the first electrode 721 located in the front side 701 of the electronic device 700 and the third electrode 731 located in the rear side 702 of the electronic device 700 are used to generate electric current in the human body, and the second electrode 723 located in the front side 701 of the electronic device 700 and the fourth electrode 733 located in the rear side 702 of the electronic device 700 are used to measure a voltage value and measure a resistance value of the human body.

The GSR may be an autonomic nervous function tests called a galvanic skin reflex. The electronic device 700 may use two adjacent electrodes to measure the GSR The first electrode 721 and second electrode 723 located in the front side 701 of the electronic device 700 or the third electrode 731 and fourth electrode 733 located in the rear side 702 of the electronic device 700 may be used to measure the GSR.

The electronic device 700 may use the two electrodes 721 and 723 of the front side 701 and the two electrodes 731 and 733 of the rear side 702 as charging ports. When the electrode 721, 723 of the front side 701 and the electrode 731, 733 of the rear side 702 are used as the charging ports, each electrode 721, 723 or 731, 733 may be used in charging by being connected to the PMIC 780.

The optic sensors 740 and 745 may be included in such a manner that at least one of them are respectively disposed to the front side 701 and rear side 702 of the housing.

According to one exemplary embodiment, the front optic sensor 740 may include an LED, an IR sensor, and a photodiode (PD). The front optic sensor 740 may be used to measure a heartbeat and a blood oxygen saturation (SpO2). For example, when the front optic sensor 740 is touched by a finger of the user, the electronic device 700 may use the LED and the PD to measure a photoplethysmogram (PPG) signal and thus acquire heartbeat information, and at the same time, may use the IR sensor together to acquire blood oxygen saturation (SpO2) information.

The rear optic sensor 745 may include the LED and the PD. The rear optic sensor 745 may be used in an always-on measurement of the heartbeat. When the electronic device 700 (e.g., the write-type wearable device) is worn by the user, the rear optic sensor 745 is in contact with a wrist surface in a direction of the back of a hand. As a result, the PPG signal may be measured, and heartbeat information may be derived through the PPG signal. The heartbeat information may be obtained continuously while the electronic device 700 is worn by the user.

The front optic sensor 740 may be located between the two electrodes 721 and 723 located in the front side 701 to simultaneously measure a variety of biometric information. The adjacent two electrodes 721 and 723 and the front optic sensor 740 may be disposed to be able to simultaneously measure one finger.

The display 750 may be located in the front side 701 of the electronic device 700 and consist of elements such as an OLED, a Quantum LED (QLED), or an LCD. Alternatively, the display 750 may include the LED configured to be capable of displaying simple information. The electronic device 700 may provide the user with a variety of information such as a date, a time, or a battery charging amount by displaying the information through the display 750. The display 750 may provide the user with related health information (e.g., a guide, a measurement result, and a chart) by displaying the information on the basis of biometric information measured based on at least one part of the electrodes 721, 723 and 731, 733 and the optic sensors 740 and 745.

The processor 760 may control an overall operation of the electronic device 700. The processor 760 may have the same or similar structure of the processor 120 of FIG. 1 or the AP 210 of FIG. 2. Several types of processors may be equipped in the processor 760 based on performance and efficiency. The processor 760 may be implemented by an AP used for high performance or a micro (or low power) processor (e.g., a micro controller unit (MCU)) of which performance is lower than the AP but is capable of low power processing. The MCU may be expressed by a sensor hub, a supplementary processor, or a bio-processor (BP).

The processor 760 may manage and process driving of an algorithm for converting a signal measured by each sensor 765 into meaningful biometric information and an overall driving order of the electronic device 700. The processor 760 and the sensor controller 770 may be configured as one module, or may be configured as independent modules.

The processor 760 may determine whether the battery 785 is charged through the battery charging module (or a charging circuit). The processor 760 may process an operation related to obtaining biometric information by using a first method (e.g., a measurement based on a normal mode and a low power mode) through a bio-sensor (e.g., the front electrode 721, 723, the front optic sensor 740, the rear electrode 731, 733, and the rear optic sensor 745) if the battery 785 is not charged, and acquiring the biometric information by using a second method (e.g., a measurement based on an enhanced mode and a precise mode) through the bio-sensor if the battery is charged.

The first method may include changing persistency of a measurement period, computation period, or measurement time related to obtaining the biometric information according to a first setting in response to a low power mode (or a normal mode), and obtaining the biometric information according to the first setting by using at least one part of the front electrode 721, 723 or the rear electrode 731, 733.

The second method may include changing the measurement period, computation period, or measurement time related to obtaining of the biometric information according to a second setting in response to a precise mode (or an enhanced mode), and obtaining the biometric information according to the second setting by using the rear electrode 731, 733.

The low power mode (or the normal mode) may include a mode for obtaining the biometric information with the first setting (e.g., first power consumption, minimum power) configured by considering a usage time of the electronic device 700 in a state where the battery 785 is not charged through the front electrode 721, 723. The precise mode (or the enhanced mode) may include a mode for obtaining the biometric information with the second setting (e.g., second power consumption, maximum power) configured in a state where the battery 785 is charged through the front electrode 721, 723.

The processor 760 may measure biometric information by setting the persistency of the measurement time to be short and/or the measurement period to be long according to the first setting. The processor 760 may measure the biometric information by setting the persistency of the measurement time to be long and/or the measurement period to be short according to the second setting.

The sensor controller 770 may play a role of adjusting an operation of the various sensors 765 equipped in the electronic device 700. The sensor controller 770 may be controlled by the processor 760, and may be operatively coupled with the sensor 765. The sensor controller 770 may be connected with the sensor 765 (e.g., an acceleration sensor), the electrodes 721, 723 and 731, 733, or the optic sensors 740 and 745, and a circuit configured under the control of the processor 760 may be driven to measure biometric information through the electrodes.

The memory 775 may be connected to the processor 760 to store information collected from the sensor 765.

The memory 775 may store one or more programs, data, or instructions related to the AP 210 configured for determining whether to charge the battery 785 through a charging circuit (e.g., the battery charging module 780), and if the battery 785 is not charged, acquiring biometric information by using the first method through a bio-sensor (e.g., the front electrode 721, 723, the front optic sensor 740, the rear electrode 731, 733, and the rear optic sensor 745), whereas if the battery is charged, acquiring the biometric information by using the second method through the bio-sensor.

The PMIC (or the charging circuit) 780 may play a role of supplying power of the internal battery 785 to the sensor 765 and each module when the electronic device 700 is not charged. While the electronic device 700 is charged, the battery charging module 780 may charge the internal battery 785 by delivering electric current applied from the charging electrode 791, 793 (or the electrode 721, 723) to the internal battery 785. The battery charging module 780 may supply power to the sensor 765 of the electronic device 700 during the charging.

The battery charging module 780 connected to the electrodes 721, 723 and 731, 733 may perform the charging through the electrodes 721, 723 and 731, 733. The battery charging module 780 may be connected to the front electrode 721, 723 (e.g., the first electrode 721 and the second electrode 723) mounted to the front side 701, the rear electrode 731, 733 (e.g., the third electrode 731 and the fourth electrode 733) mounted to the rear side 702, and each of the electrodes 721, 723 and 731, 733 may be respectively designated as a positive (+) electrode (e.g., the first electrode 721 and the third electrode 731) and a negative (−) electrode (e.g., the second electrode 723 and the fourth electrode 733).

The battery charging module 780 may control power consumed in the electronic device 700, and may control an operation of the electronic device 700 during the charging. The battery charging module 780 may configure a circuit by using at least one of electrodes to which power is supplied between the front electrode 721, 723 connected to the front side 701 and the rear electrode 731, 733 connected to the rear side 702. Which electrode will be used between the front electrode 721, 723 and the rear electrode 731, 733 to configure the circuit for charging may be controlled by the battery charging module 780.

The charging electrode 791, 793 (e.g., a first charging electrode 791 and a second charging electrode 793) configured in the rear side 702 by the electronic device 700 may be omitted when charging is performed through the front electrode 721, 723 of the front side 701 or the rear electrode 731, 733 of the rear side 702.

The battery 785 includes an element for storing electricity. The battery 785 may charge or discharge electricity under the control of the battery charging module 780. The battery 785 may include a positive pole and a negative pole. The battery 785 may include a charging-type battery and/or a solar battery.

The communication module 755 may include all or some parts of the communication module 220 of FIG. 2. The communication module 755 may play a role of transmitting measured biometric information to an external device (e.g., the electronic devices 102 and 104 or the server 106 of FIG. 1). The external device may include a computer, a server, a smart phone, and peripheral devices. A communication method that can be utilized in the electronic device 700 may be bluetooth, BLE, WiFi, 3G, or LTE.

The electronic device 700 (e.g., the wrist-type health wearable device) may provide at least two types of health information acquisition methods according to a measurement period and a measurement scheme.

A first health information acquisition scheme may be a user demand measurement scheme (or an on-demand measurement scheme) for utilizing the front electrode 721, 723 of the front side 701 and the front optic sensor 740 of the front side 701. In the on-demand measurement scheme, when a user who intends to perform a measurement touches a sensor (e.g., the front electrode 721, 723 and the front optic sensor 740) by using a finger, the measurement may be performed by detecting this. Health information acquired by using the on-demand measurement scheme may include information such as instantaneous heart rate (HR) information, SpO2 information, BIA information, and GSR information that can be measured for a relatively short period of time.

A second health information acquisition scheme may be a regular measurement scheme (or an always-on measurement scheme) for utilizing the rear electrode 731, 733 of the rear side 702 and the rear optic sensor 745 of the rear side 702. In the always-on measurement scheme, a measurement may start when the user wears the electronic device 700, and health information may be continuously acquired while the user wears the electronic device 700. The health information acquired by using the always-on measurement scheme may be utilized in a function requiring continuous health information such as acquiring continuous HR information, sleep time information, sleep efficiency information, or resting HR information.

The electronic device for the user's health care may have a purpose of persistently detecting a user's physical state or health state for 24 hours. However, in case of the conventional technique, charging can be performed only when the electronic device (e.g., the wrist-type health wearable device) is separated from a wrist for charging. Accordingly, the on-demand measurement scheme and the always-on measurement scheme are both impossible when the electronic device is being charged. As a result, there may be a limitation that continuity of the health information cannot be maintained since user's health information cannot be acquired while the electronic device is being charged.

The battery charging module 780 may be connected to the front electrode 721, 723 of the front side 701 and the real electrode 731, 733 of the rear side 702. Accordingly, an embodiment of the present disclosure provides a method in which not only the charging electrode 791, 793 of the rear side 702 for charging but also an electrode (e.g., the front electrode 721, 723 and the rear electrode 731, 733) used for measuring a bio-signal are used to charge a battery. When applying such a method, the on-demand measurement scheme in which the front electrode 721, 723 of the front side 701 is used when the battery 785 of the electronic device 700 is charging may be limited, but the always-on measurement scheme in which the rear electrode 731, 733 of the rear side 702 and the rear optic sensor 745 are used may be performed simultaneously with the charging. In addition, sufficient power may be supplied from the front electrode 721, 723 of the front side 701. Therefore, a period of acquiring health information can be shortened in the always-on measurement, thereby significantly increasing the accuracy of continuous health information measured by using the always-on measurement scheme.

The electronic device according to various embodiments of the present disclosure includes the battery 785, the charging circuit (e.g., the battery charging module 780) for charging the battery 785, the bio-sensor (e.g., the front electrode 721, 723, the front optic sensor 740, the rear electrode 731, 733, or the rear optic sensor 745), and the processor 760. The processor 760 may be configured to determine whether the battery 785 is being charged through the charging circuit, if the battery 785 is not being charged, acquire biometric information by using a first method through the bio-sensor, and if the battery 785 is being charged, acquire the biometric information by using a second method through the bio-sensor.

According to an embodiment of the present disclosure, the electronic device may include a measuring circuit for inputting a signal by an external device or a user. The measuring circuit may be selectively connected to the charging circuit or the bio-sensor.

According to an embodiment of the present disclosure, the measuring circuit may include at least one front electrode located in a front side of the electronic device, and at least one rear electrode located in a rear side of the electronic device.

According to an embodiment of the present disclosure, the electronic device may include at least one switch for selectively connecting the measuring circuit to the charging circuit or the bio-sensor.

According to an embodiment of the present disclosure, the processor may be configured to, if the battery is not being charged, connect the front electrode to the bio-sensor by using the switch, and if the battery is being charged, connect the front electrode to the charging circuit by using the switch.

According to an embodiment of the present disclosure, the rear electrode may be electrically connected to the bio-sensor.

According to an embodiment of the present disclosure, the processor may be configured to detect a charging signal related to charging of the battery through the front electrode, connect the front electrode to the charging circuit on the basis of the detecting of the charging signal, charge the battery by using the front electrode, and acquire the biometric information by using the rear electrode.

According to an embodiment of the present disclosure, the first method may include changing persistency of a measurement period, computation period, or measurement time related to obtaining the biometric information according to a first setting in response to a low power mode, and obtaining the biometric information according to the first setting by using the front electrode or the rear electrode. The second method may include changing the measurement period, computation period, or measurement time related to obtaining the biometric information according to a second setting in response to a precise mode, and obtaining the biometric information according to the second setting by using the rear electrode.

According to an embodiment of the present disclosure, the processor may be configured to detect a bio-signal through the front electrode, connect the front electrode to the bio-sensor on the basis of the detecting of the bio-signal, and acquire the biometric information by using the front electrode and the rear electrode.

According to an embodiment of the present disclosure, the processor may set the measuring circuit to a standby state if the battery is not being charged by using the measuring circuit.

The measuring circuit may generate an interrupt corresponding to a user's touch in the standby state or mounting of an external device.

According to an embodiment of the present disclosure, the processor may be configured for disconnecting a front electrode of the measuring circuit from the charging circuit and the bio-sensor in the standby state of the measuring circuit.

According to an embodiment of the present disclosure, the processor may be configured to detect the interrupt through a front electrode of the measuring circuit in the standby state of the measuring circuit, and selectively connect the front electrode to the charging circuit or the bio-sensor in response to the interrupt.

Figure 8:
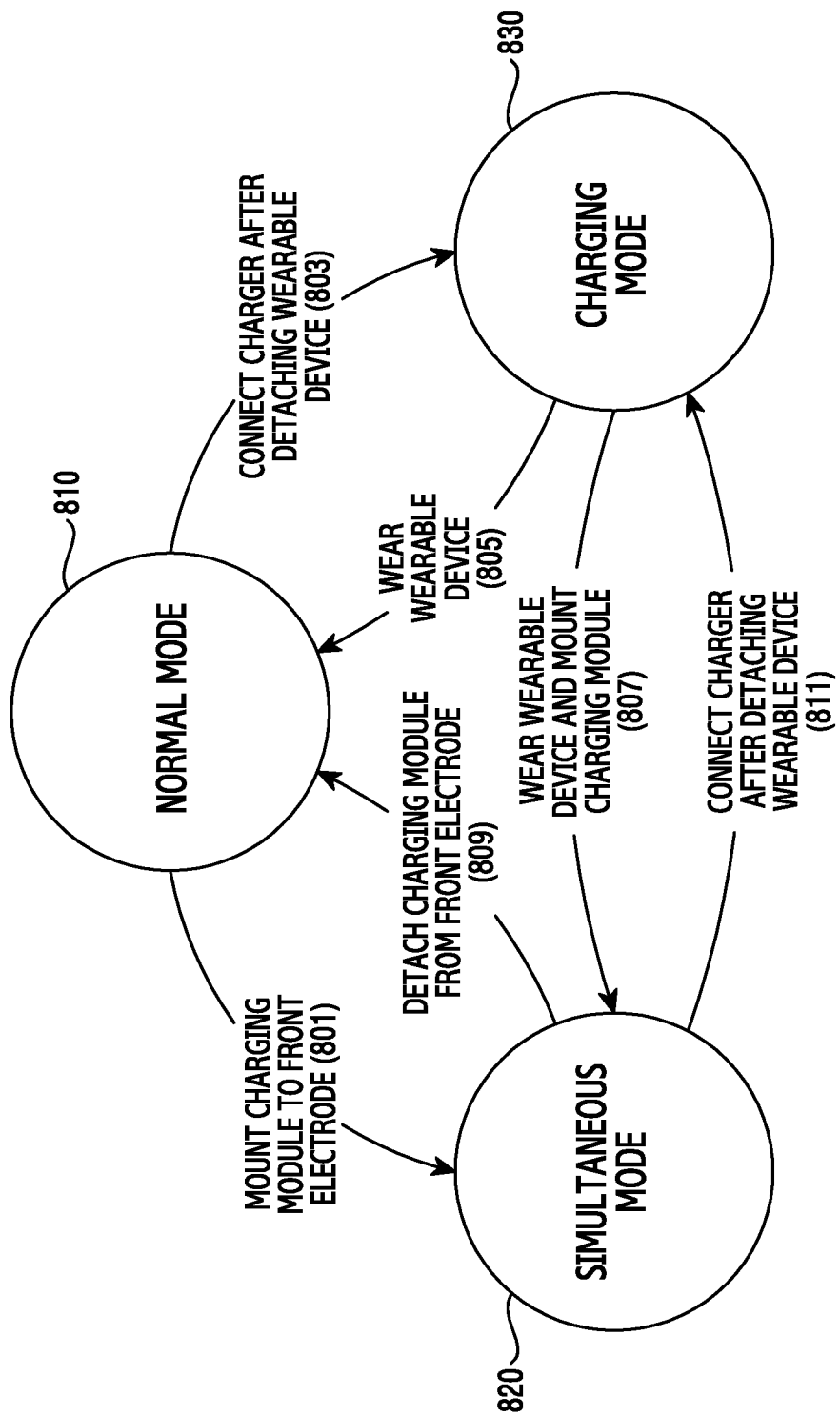
FIG. 8 illustrates an operation mode of an electronic device, according to an embodiment of the present disclosure.

FIG. 8 illustrates an operation mode of an electronic device, according to an embodiment of the present disclosure.

Referring to FIG. 8, an electronic device (e.g., the wrist-type wearable device) may roughly include three operation modes. For example, the electronic device 700 may operate based on a normal mode 810, a charging mode 820, and a simultaneous mode 830.

The normal mode 810 may represent a mode in which an on-demand measurement and an always-on measurement are both possible in a state where a user wears the electronic device 700. Since the electronic device 700 uses the internal battery 785 of the electronic device 700 to perform the measurement in the normal mode 810, the battery 785 of the electronic device 700 may be discharged when a usage time is continued. In the normal mode 810, a period of measuring, health information may be applied as a long period of time in the always-on measurement in order to ensure a long usage time of the electronic device 700.

While operating in the normal mode 810, in step 801, the electronic device 700 may operate by switching from the normal mode 810 to the simultaneous mode 820 when a charging module is mounted to the front electrode 721, 723 of the front side 701. While operating in the normal mode 810, in step 803, the electronic device 700 may operate by switching from the normal mode 810 to the charging mode 830 when a charger is connected after the electronic device 700 is detached from a user.

The simultaneous mode 820 may correspond to a case where the charging module is mounted to the front electrode 721, 723 of the electronic device 700 in a state where the user wears the electronic device 700, and may indicate a mode in which measuring and charging can be performed simultaneously. The electronic device 700 may use the front electrode 721, 723 in the charging of the internal battery 785 of the electronic device 700 through a charging module in the simultaneous mode 820, and the on-demand measurement using the front electrode 721, 723 may be limited. On the other hand, sufficient power may be supplied to the electronic device 700 in a large capacity battery included in the charging module, and thus the electronic device 700 may perform the always-on measurement of a short measurement period. The electronic device 700 may provide always-on health measurement information with high accuracy since the always-on measurement is supported with the short period of time. While operating in the simultaneous mode 820, in step 809, the electronic device 700 may operate by switching from the simultaneous mode 820 to the normal mode 810 when the charging module is detached from the front electrode 721, 723. While operating in the simultaneous mode 820, in step 811, the electronic device 700 may operate by switching from the simultaneous mode 820 to the charging mode 830 when the charger is connected after the electronic device 700 is detached from the user.

The charging mode 830 may represent a mode in which the user charges the electronic device 700 through the charger (or a charging cradle) by detaching the electronic device 700. The charging mode 830 may represent a mode in which the battery 785 of the electronic device 700 is charged on the basis of power supplied from the charger through the charging electrode 791, 793 or the rear electrode 731, 733 of the rear side 702 of the electronic device 700. The charging mode 830 may be a state where the user separates the electronic device 700 from a user's body, and in general, biometric information may not be able to be measured in this case. The electronic device 700 may not be able to perform the always-on measurement in the charging mode 830, but may be able to perform the on-demand measurement. For example, in a case of switching to the charging mode 830 according to step 803, the electronic device 700 may measure biometric information in the charging mode 830 according to a user's demand on the basis of the front electrode 721, 723 of the front side 701. In a case of switching to the charging mode 830 according to step 811, if the charging module is mounted to the electronic device 700 in the charging mode 830, charging may be achieved simultaneously on the charging module and the internal battery 785 of the electronic device 700. When the charging module is mounted to the front electrode 721, 723 of the electronic device 700, the front electrode 721, 723 may be used to charge not only the internal battery 785 of the electronic device 700 but also an internal battery of the charging module together.

While operating in the charging mode 830, the electronic device 700 may operate by switching from the charging mode 830 to the normal mode 810, in step 805, or the simultaneous mode 820, in step 807, when the electronic device 700 is disconnected from the charger and is worn by the user. The electronic device 700 may operate by switching to the normal mode 810 or the simultaneous mode 820 according to whether the charging module is mounted.

The front electrode 721, 723 of the front side 701 may be used in the on-demand measurement such as ECG, BIA, or GSR. Accordingly, in a normal case, it may be configured such that biometric information is measured when a part of a human body, such as a user's finger, is connected (or in contact) with the front electrode 721, 723. It is possible to operate in the simultaneous mode in which measuring and charging can be simultaneously performed by automatically detecting a specific voltage value or a signal of a specific pattern in the front electrode 721, 723 (e.g., the first electrode 721 and the second electrode 723) of the front side 701.

FIG. 9A, FIG. 9B, FIG. 9C, FIG. 9D, and FIG. 9E illustrate a mode change scenario in an electronic device, according to various embodiments of the present disclosure.

Figure 9A:
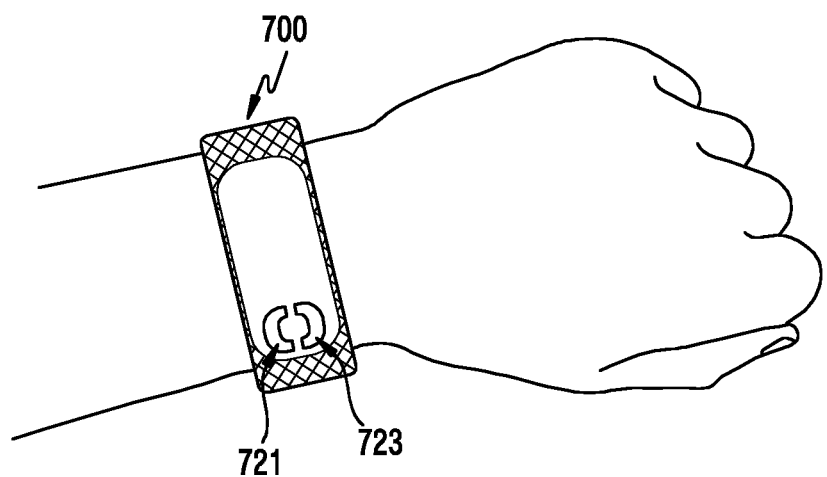
FIG. 9A, FIG. 9B, FIG. 9C, FIG. 9D, and FIG. 9E illustrate a mode change scenario in an electronic device, according to an embodiment of the present disclosure.
Figure 9B:
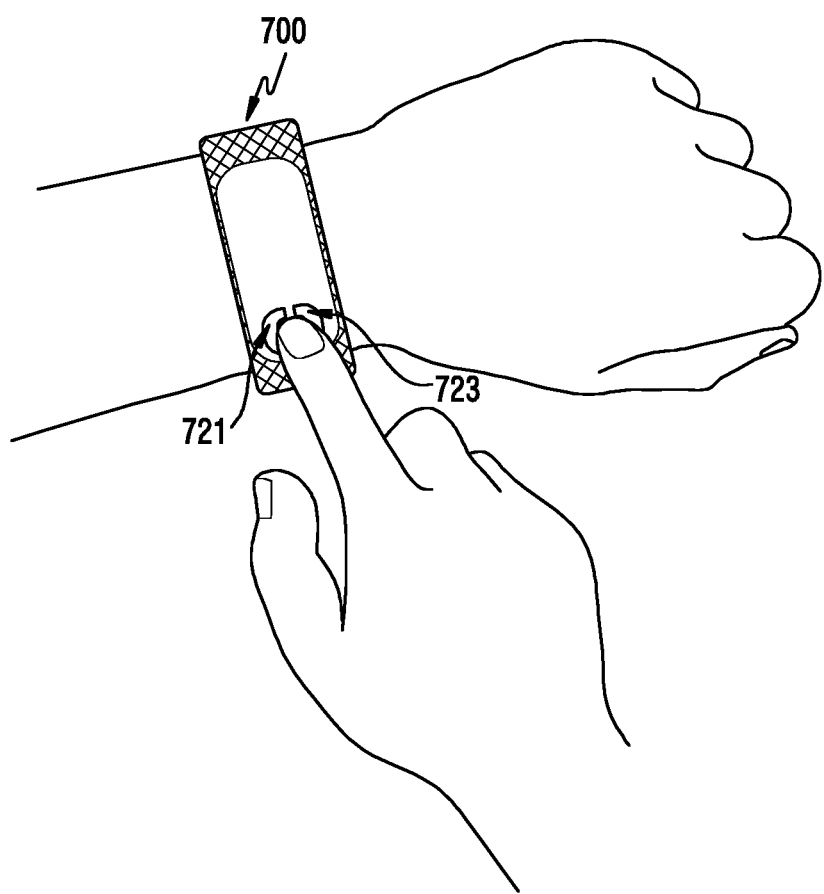
Figure 9C:
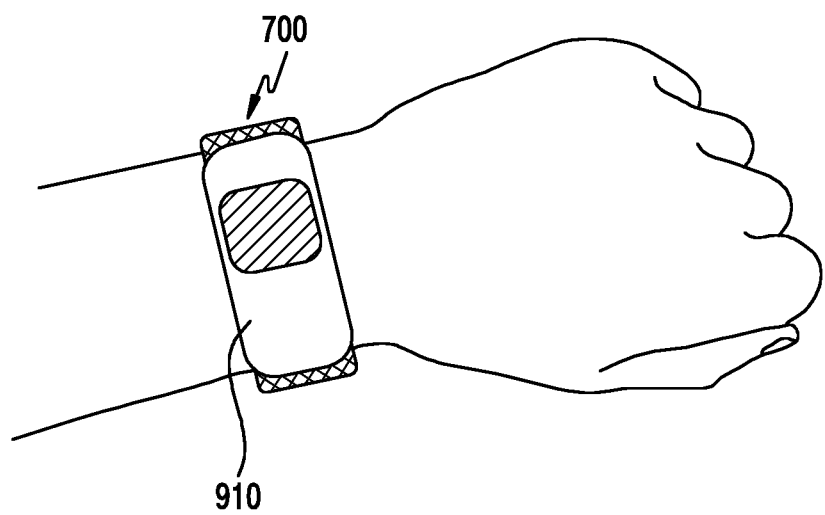
Figure 9D:
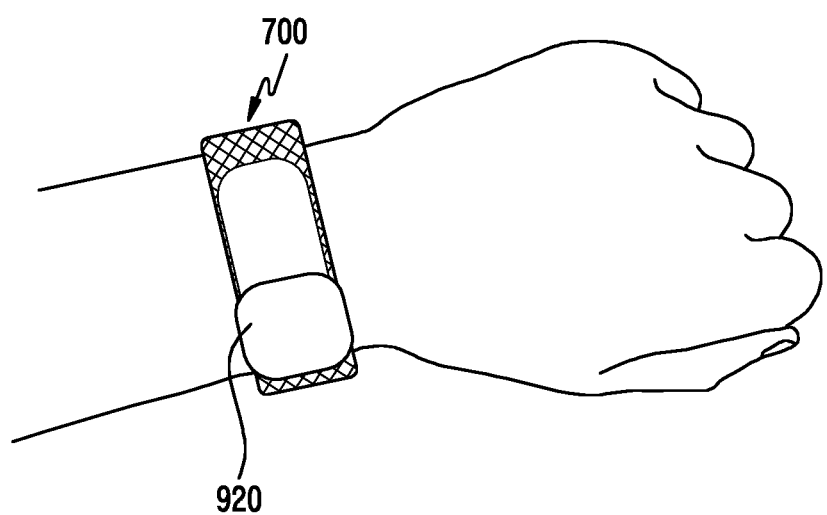
Figure 9E:
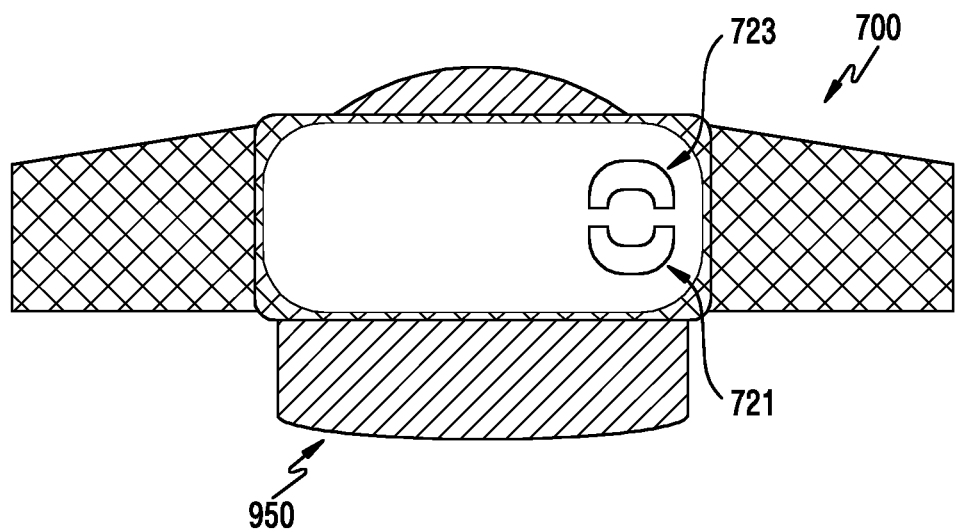

As shown in FIG. 9A, FIG. 9B, FIG. 9C, FIG. 9D, and FIG. 9E, a mode change scenario based on a charging state in the electronic device 700 is illustrated. FIG. 9A illustrates a state where the electronic device 700 operates in a normal mode, and FIG. 9B illustrates performing an on-demand measurement scheme by a user in the normal mode. FIG. 9C and FIG. 9D illustrate a state where the electronic device 700 operates in a simultaneous mode, and FIG. 9E illustrates a state where the electronic device 700 operates in a charging mode.

Referring to FIG. 9A, the electronic device 700 is a wrist-type wearable device and operates in a normal mode. The electronic device 700 may be in a state of being worn on a user's wrist. In the normal mode, the electronic device 700 may detect an HR or a movement (e.g., a motion or an activity) in a background.

In the normal mode, the front electrode 721, 723 of the electronic device 700 may perform sensing based on a user's intention. For example, an HR measurement, an SpO2 measurement, or a stress measurement, may be performed through the front electrode 721, 723.

The measurement through the front electrode 721, 723 may be an on-demand measurement scheme. The on-demand measurement scheme may provide a more reliable measurement state than a measurement using a rear electrode. In particular, the on-demand measurement scheme may be regarded to have a higher reliability measurement value than a background measurement based on the rear electrode. In addition a scenario in which at least three electrodes are required may be provided when user's biometric information is measured. For example, an ECG measurement is to measure an electrocardiogram generated from a heart may require three electrodes. In addition, a BIA measurement for measuring a body fat may require four electrodes in total, and may allow electric current to flow with an impedance corresponding to a human body to measure a body fat ratio. Therefore, the front electrode 721, 723 and the rear electrode may be utilized to provide various measurements.

In a state where the user wears the electronic device 700, as shown in FIG. 9A, regular biometric information may be measured through an always-on measurement scheme. In addition, in the always-on measurement scheme, as shown in FIG. 9B, biometric information may be measured in such a manner that the user touches the front electrode 721, 723 of the electronic device 700 by using a finger. When the user touches the front electrode 721, 723 by using the finger, a heartbeat may be measured by using an optic sensor (e.g., a PPG sensor). An ECG, a GSR, or a BIA, may be measured by using the front electrode 721, 723 of the front side 701 with which an index finger is in contact with, and the rear electrode 731, 733 with which a part of a back of a hand or a wrist is in contact.

In the normal mode, the rear electrode 731, 733 (e.g., the third electrode 731 and the fourth electrode 733) of the rear side 702 of the electronic device 700 and the rear optic sensor 745 may be used in the always-on measurement, and the front electrode 721, 723 (e.g., the first electrode 721 and the second electrode 723) of the front side 701 of the electronic device 700 may be used as a sensor for the on-demand measurement. In the normal mode, the first electrode 721 and the second electrode 723 may be operatively coupled to the sensor controller 770, and an operation of the sensor may be driven by the processor 760.

Referring to FIG. 9C and FIG. 9D, a state where the electronic device 700 operates in a simultaneous mode for simultaneously performing charging and measuring using a first charging module 910 or a second charging module 920. For example, FIG. 9C illustrates when the first charging module 910 is mounted in a shape of entirely covering the front side 701 of the electronic device 700, and FIG. 9D illustrates when the second charging module 920 is mounted in a shape of partially covering the front side 701 of the electronic device 700.

The first charging module 910 exemplified in FIG. 9C may include a device capable of charging the electronic device 700 without an additional wired connection with a charger. The second charging module 920 exemplified in FIG. 9D may include a device capable of charging the electronic device 700 in a state of being connected to the charger in a wired manner by using a cable (e.g., a cable 1070 of FIG. 10B). The electronic device 700 may be charged in a state of not being connected to the charger in the wired manner even by the second charging module 920 (e.g., the cable is detachable from the second charging module 920).

When the electronic device 700 operates in the simultaneous mode by mounting the first charging module 910 or the second charging module 920 thereto, the front electrode 721, 723 may be connected to the first charging module 910 or the second charging module 920, and charging may be performed through the front electrode 721, 723. In this case, the rear electrode 731, 733 may perform the measurement in a background, and may measure a heartbeat or a GSR.

Since the electronic device 700 performs charging through the front electrode 721, 723, a measurement of a BIA or an ECG may be limited, and an on-demand measurement may also be limited according to a measurement type. However, the electronic device 700 may increase a measurement accuracy and efficiency as to a measurement of a rear side by using the rear electrode 731, 733. A heartbeat which has been measured with a period of 10 minutes may be measured by the electronic device 700 with a period of 1 minute since power is persistently supplied on the basis of the first charging module 910 or the second charging module 920.

According to an embodiment of the present disclosure, it is important to ensure a long usage time (e.g., at least one week) due to a characteristic of the electronic device 700. When a measurement period is decreased, electric current consumption is increased, thereby decreasing the usage time. However, a heartbeat may be more precisely measured on the basis of an enhanced mode (or a precise mode) during charging based on external power. For example, when a great amount of data is collected to measure the heartbeat, not only the heartbeat can be traced more precisely but also accuracy of a sleep efficiency measurement can be increased during the sleep of the user. In addition, even in case of measuring a stress or an oxygen saturation, data may be collected more precisely by setting a measurement period to be short, and reliability may be increased in a symptom checker.

Further, in addition to the existing acceleration sensor, a motion measurement can be achieved more precisely on the basis of various sensors such as 6-axis or 9-axis sensors gyroscopes, magnetic sensors, or barometers. Accordingly, a state and movement of the electronic device 700 can be more closely determined, and a fine and precise state such as sleep detection can be measured through transmission and reception with respect to peripheral devices.

As exemplified in FIG. 9C and FIG. 9D, when the electronic device 700 operates in the simultaneous mode, the front electrode 721, 723 is electrically connected to the first charging module 910 or the second charging module 920, and thus may receive power supplied from the first charging module 910 or the second charging module 920 and may display a result value for the enhanced mode through the display 760. Although the display 750 may occupy a great portion of electric current consumption, it is possible to display various information by continuously supplying power by means of the charging module 910, 920. In addition since the electronic device 700 may have a short update period through BT or WiFi, by means of the communication module 755, the electronic device 700 can be effectively used.

FIG. 9E illustrates a state where the electronic device 700 is connected to a charger (or a cradle) 950 to be charged in a state of operating in a charging mode. The charging mode may be a primary charging state having a higher priority than a secondary charging state by means of the first charging module 910 or the second charging module 920. The electronic device 700 may be in a state of being detached from a user in the charging mode, and may perform charging through the rear electrode 731, 733 (or the charging electrode 791, 793). When the front electrode 721, 723 is charged (e.g., in a state where the first charging module 910 or the second charging module 920 is mounted) during charging through the rear electrode 731, 733, the first charging module 910 or the second charging module 920 may be charged through the front electrode 721, 723, and may be controlled such that the charging is not performed by the front electrode 721, 723 according to a configuration of the electronic device 700.

Even if the electronic device 700 operates in the charge mode, as shown in FIG. 9E, an on-demand measurement using the front electrode 721, 723 may be provided. In order to more precisely measure biometric information, a measurement performed by the front electrode 721, 723 may be limited in the charging mode. For example, since information of a person other than the user may be provided as user's health information for being measured during charging, the electronic device 700 may be configured to perform the on-demand measurement only in a state where the user wears the electronic device 700. When the electronic device 700 operates in the charging mode, the front electrode 721, 723 may be used by being replaced with a button during charging, and may be allowed to display information required in the display 750 or to change a menu.

Figure 10A:
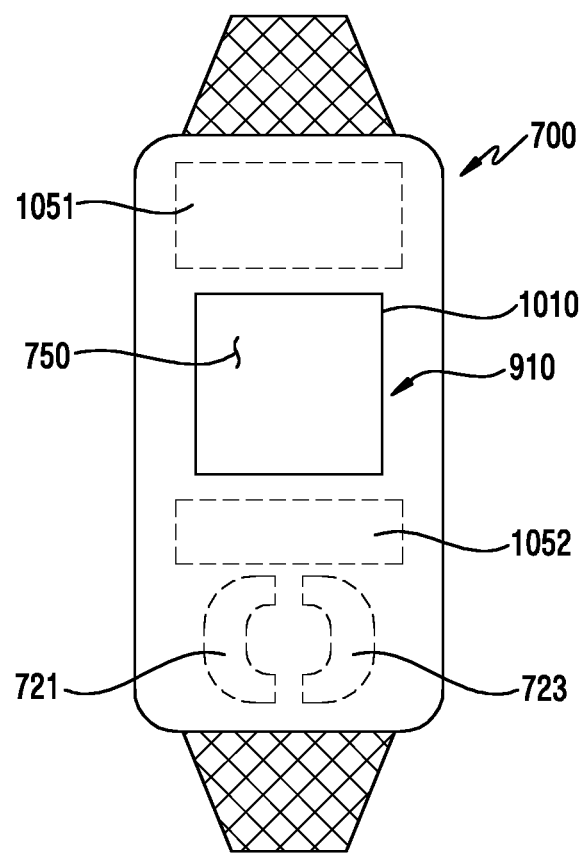
FIG. 10A and FIG. 10B illustrate an operation based on a simultaneous mode in an electronic device, according to an embodiment of the present disclosure.
Figure 10B:
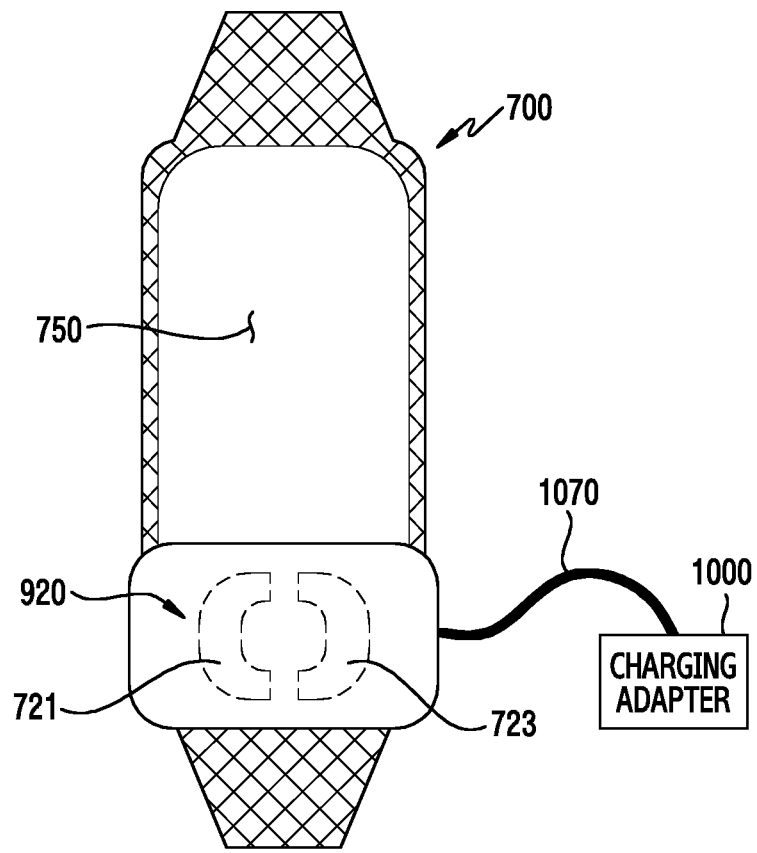

FIG. 10A and FIG. 10B illustrate an operation based on a simultaneous mode in an electronic device according an embodiment of the present disclosure.

Referring to FIG. 10A and FIG. 10B, the charging module (e.g., the first charging module 910 or the second charging module 920) may be mounted to the rear electrode 702 (e.g., the first electrode 721 and the second electrode 723 located in the front side 701 of the electronic device 700 to constantly provide an always-on measurement by using the rear optic sensor 745 or the rear electrode 731, 733 (e.g., the third electrode 731 and the fourth electrode 733) located in the rear side 702 while charging the electronic device 700.

FIG. 10A illustrates an example of a case where the charging module mounted to the electronic device 700 is the first charging module 910. As shown in FIG. 10A, the charging module may have a form of a cradle including an internal battery (e.g., a first battery 1051 and a second battery 1052) of the charging module. The charging module may have a structure in which at least one part of the display 750 is not covered so that a remaining capacity or time of the battery 785 of the electronic device 700 can be confirmed through the display 750 of the electronic device 700 even in a state of being mounted to the electronic device 700. As indicated by a reference number 1010, any one side of the cradle of the charging module may be configured to be transparent or may be configured in a perforation state.

When the charging module is mounted, the electronic device 700 may operate in the simultaneous mode for simultaneously performing measuring and charging. Since the charging module is mounted to the electronic device 700 in a state where the electronic device 700 is worn by the user, the electronic device 700 may operate in the simultaneous mode when a reference voltage based on the charging module 910 is applied through the front electrode 721 or 723.

The charging module may charge the battery (e.g., a first battery 1051 and a second battery 1052) of the charging module through wired charging or wireless charging by means of an external charger when the electronic device 700 is being charged or not being charged.

When the charging module is connected, the electronic device 700 may use power of the battery (e.g., a first battery 1051 and a second battery 1052) of the charging module to charge the battery 785 of the electronic device 700. When a weight of the electronic device 700 is not much burdened such as during sleep of the user, the electronic device 700 simultaneously performs charging of the electronic device 700 while measuring biometric information, and thus the biometric information can be continuously measured. In addition, since power can be sufficiently provided from the charging module to the electronic device 700, the electronic device 700 can set a measurement period of an always-on measurement, thereby significantly improving accuracy of heath information of the always-on measurement.

The charging module may be fixed through a groove in a lateral side of the housing of the electronic device 700, and may be connected to a charging port of the charging module and the front electrode (e.g., the first electrode 721 and the second electrode 723) of the electronic device 700 to perform charging. The electronic device 700 may confirm that it is in a charging state when a power source (e.g., a reference voltage) or a predefined signal is applied through the front electrode, and may be allowed to perform charging by releasing a connection at the sensor controller 700 and by connecting the charging module and the battery charging module 780.

If the charging module is connected to the electronic device 700, the health information of the always-on measurement may be performed more precisely than a normal mode of the electronic device 700. For example, the electronic device may measure information such as a heartbeat, sleep, stress, or SpO2, that can be always measured in a background with a frequent period (e.g., a short period) through a sensor such as the rear optic sensor 745 and/or the rear electrode 731, 733 located in the rear side 702 of the electronic device 700. In addition, the electronic device 700 may be updated more frequently also in wireless communication such as WiFi or bluetooth, and efficiency of the memory 775 of the electronic device 700 may be increased due to sensor batching.

Referring to FIG. 10B, FIG. 10B illustrates a case where the charging module mounted to the electronic device 700 is the second charging module 920. In FIG. 10B, a case where the second charging module 920 does not include an internal battery is shown. The charging module may have a form of a cradle connected to a charging adapter 1000 in a wired manner as shown in FIG. 10B. The second charging module 920 may be implemented to be mounted to the front side 701 of the electronic device 700 in a state of being connected to the charging adapter 1000. Alternatively, the charging module may provide charging as a connection through a USB.

The charging module for wired charging may be configured in a single type such as a travel adapter (TA) for normal charging, and may be configured in a form of a cradle connected to a micro-USB or USB-C type charger. The charging module may be fixed to a lateral side of the housing of the electronic device 700 through a standardized groove, and a charging port of the charging module 920 and the front electrode of the electronic device 700 may be connected to constitute a circuit for charging.

The electronic device 700 may be charged in a wired manner through the charging module, and power may be always supplied. Therefore, even when the wired-type charging module is connected, the electronic device 700 may perform a measurement through a sensor more precisely than a non-charging state while charging is performed.

The charging module (e.g., the second charging module 920) which provides charging of the electronic device 700 in a wired manner plays a role of only a connection, and thus may be not limited in size. Therefore, as shown in FIG. 10B, only one part of the display 750 may be covered by the charging module having a size corresponding to the front electrode of the front side 701 of the electronic device 700, and a variety of information, such as a charging state, may be displayed through the remaining areas not covered in the display 750. A current state of the battery 785, a type of a sensor in which a measurement is currently being performed, or a measurement result, may be immediately confirmed through the remaining areas of the display 750.

In a scenario in which the electronic device 700 is charged in a wired manner as in FIG. 10B, the user may have a stable state while a movement of the user is generally constrained. Therefore, it is possible to drive a measurement scenario in which a measurement is required when the user is in the stable state. According to an embodiment of the present disclosure, a resting HR may be measured based on a wired charging scenario when a user's heartbeat is measured. A sensing state of the user may be inferred by combining a normal measurement state, a movement of an acceleration sensor, and wired charging state information which may be utilized in correction for a more accurate measurement.

Figure 11:
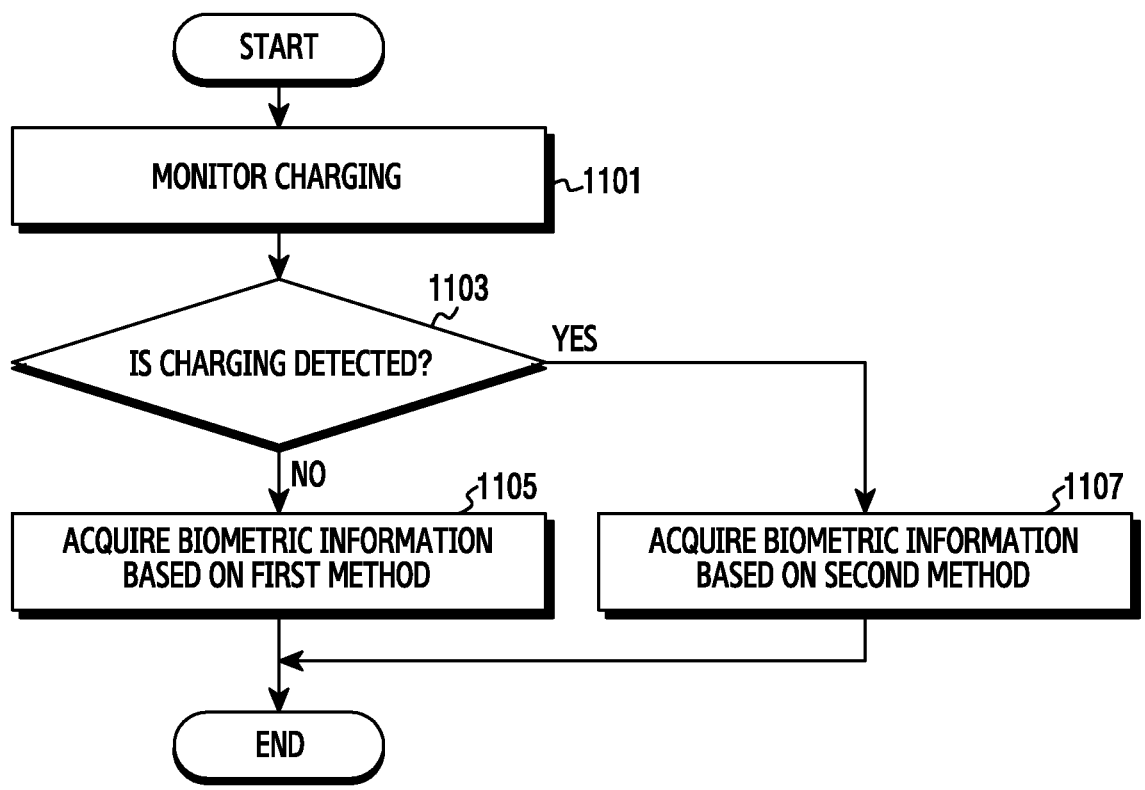
FIG. 11 is a flowchart illustrating a method of operating an electronic device, according to an embodiment of the present disclosure.

FIG. 11 is a flowchart illustrating a method of operating an electronic device, according to an embodiment of the present disclosure.

Referring to FIG. 11, in step 1101, the processor 760 of electronic device 700 monitors whether charging is performed. During the operation of electronic device 700, the processor 760 may monitor a state change such as a specific voltage or a specific signal, related to charging of the battery 785 through a charging circuit (e.g., the battery charging module 780) of the electronic device 700. The processor 760 may monitor whether the specific voltage or the specific signal is applied through the front electrode 721, 723 located in the front side 701 of the electronic device 700.

In step 1103, the processor 760 determines whether charging is detected on the basis of a monitoring result. The processor 760 may determine whether the battery 785 is being charged through the charging circuit. The processor 780 may determine whether there is an interrupt associated with charging of the battery 785 due to the front electrode 721, 723. The processor 760 may determine whether charging is performed based on the front electrode 721, 723 according to whether the specific voltage or the specific signal is applied through the front electrode 721, 723 located in the front side 701 of the electronic device 700.

If the charging of the battery 785 is not detected in step 1103 (NO in step 1103), the processor 760 acquires biometric information on the basis of a first method in step 1105. The processor 760 may operate to acquire the biometric information by using the first method (e.g., a normal mode or a low power mode) through a first sensor group (e.g., the front electrode 721, 723, the front optic sensor 740, the rear electrode 731, 733, and the rear optic sensor 745). The first sensor group may include a sensor combination (e.g., the front electrode 721, 723 and the front optic sensor 740) located in the front side 701 of the electronic device 700 and a sensor combination (e.g., the rear electrode 731, 733 and the rear optic sensor 745) located in the rear side 702 of the electronic device 700.

If the charging of the battery 785 is detected in step 1103 (YES in step 1103), the processor 760 acquires the biometric information on the basis of a second method in step 1107. The processor 760 may operate to acquire the biometric information by using the second method through a second sensor group (e.g., the rear electrode 731, 733 and the rear optic sensor 745). The second sensor group may include a sensor combination (e.g., the rear electrode 731, 733 and the rear optic sensor 745) located in the rear side 702 of the electronic device 700. The processor 760 may simultaneously perform measuring and charging on the basis of detection of battery charging by means of the front electrode 721, 723.

When the biometric information is acquired by using the second method in a simultaneous mode, the processor 760 may operate to improve accuracy of the biometric information in comparison with the first method. According to an embodiment of the present disclosure, the processor 760 may set a sensing period to be short based on the second sensor group, may set a period to be short in which the processor 760 acquires and computes the biometric information, or may set measurement power to be high of at least one sensor of the second sensor group, thereby improving sensing accuracy on the basis of at least one of those settings.

Figure 12:
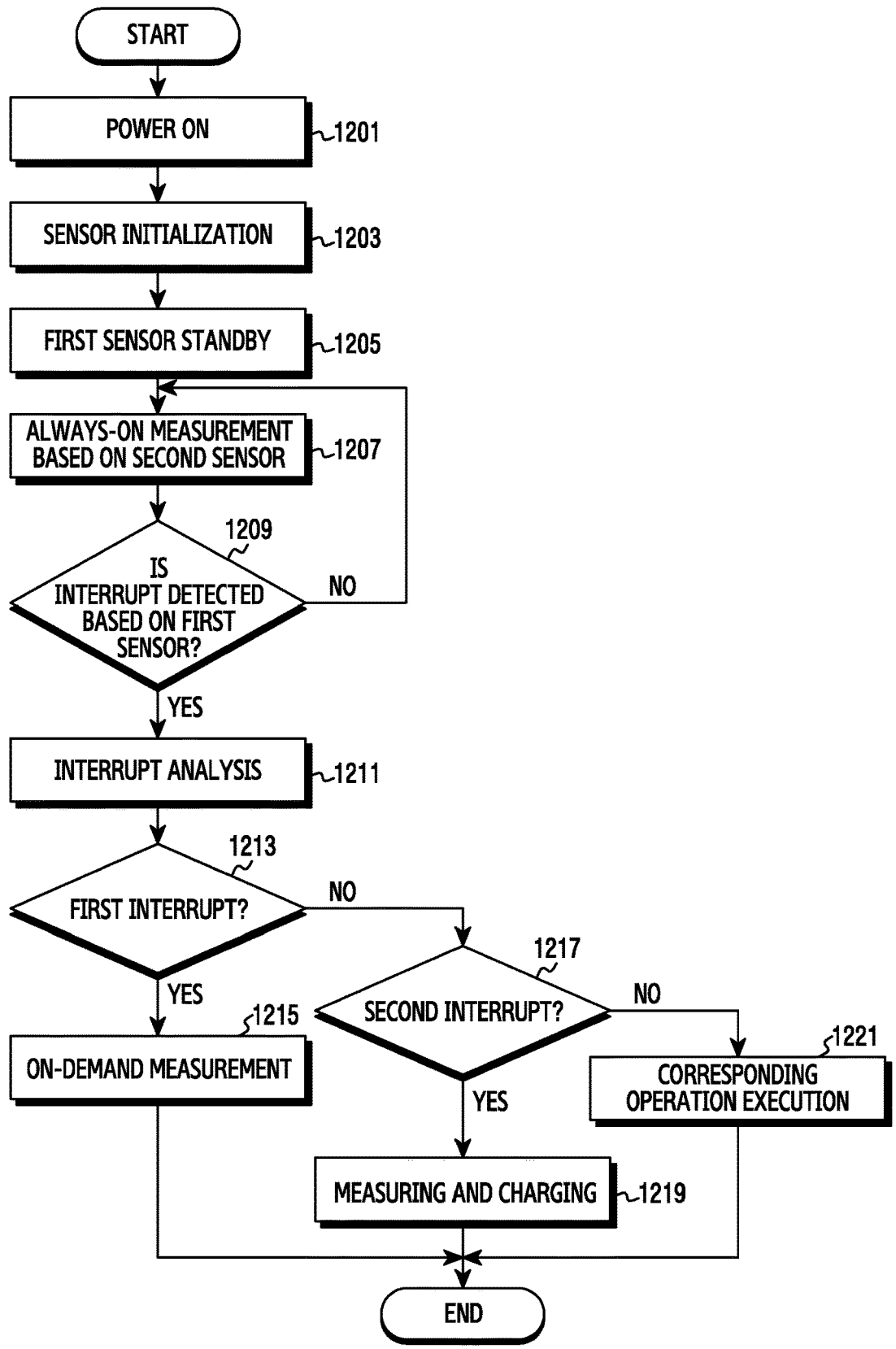
FIG. 12 is a flowchart illustrating a method of operating an electronic device, according to an embodiment of the present disclosure.

FIG. 12 is a flowchart illustrating a method of operating an electronic device, according to an embodiment of the present disclosure.

Referring to FIG. 12, in step 1201, the processor 760 of the electronic device 700 powers on the electronic device 700. The electronic device 700 may be powered on based on whether power is supplied to the electronic device 700 (e.g., an intended power-on input manipulated by a user).

In step 1203, the processor 760 performs sensor initialization based on the power-on of the electronic device 700. When the power is supplied to the electronic device 700, the processor 760 may perform an initialization process based on various sensors (e.g., the front electrode 721, 723, the front optic sensor 740, the rear electrode 731, 733, the rear optic sensor 745, and the sensor 765) related to acquiring of biometric information.

The processor 760 controls a standby of the second sensor in step 1205, and controls an always-on measurement for a first sensor in step 1207. After the sensor initialization, the processor 760 may allow the first sensor (e.g., the front electrode 721, 723 and the front optic sensor 750) located in the front side 701 of the electronic device 700 to enter a standby state and may allow a second sensor (e.g., the rear electrode 731, 733 and the rear optic sensor 745) located in the rear side 702 of the electronic device 700 to perform the always-on measurement on the basis of the second sensor recognizing that the user is wearing the electronic device 700. Steps 1205 and 1207 are not limited to the illustrated sequence of operations, and may be performed sequentially, in parallel, or in a reverse order.

The standby state of the first sensor located in the front side 701 may be for determining whether a user touches a button to use the electronic electrode 721, 723 or whether another device (e.g., a charging module) is mounted. When an electric charge is charged according to the user's touch to the front electrode 721, 723, the processor 760 may perform a bio-sensing operation by recognizing the user's touch by means of the front electrode 760 on the basis of an electric charge drop. The processor 760 may detect a touch for more than a specific period of time to filter a simple malfunction. The processor 760 may switch the first sensor back to the standby state when the bio-sensing operation is complete or when the touch for more than the specific period of time is detected.

In step 1209, the processor 760 determines whether an interrupt is detected by the first sensor. The processor 760 may determine whether a specific voltage or a specific signal is detected through the front electrode 721, 723 located in the front side 701. A separate external device may be attached to the front side 701 to detect an internal interrupt when a reference voltage (or an electric signal with a predefined pattern) is applied through the front electrode 721, 723 (or a port).

If the interrupt is not detected in step 1209 (NO in step 1209), proceeding to step 1205, the processor 760 performs operations subsequent to step 1205.

If the interrupt is detected in step 1209 (YES in operation 1209), proceeding to step 1211, the processor 760 analyzes the interrupt. The processor 760 may analyze whether the interrupt corresponds to a first interrupt of a bio-signal or a second interrupt of a charging signal (e.g., a reference voltage or an electric signal with a predefined pattern). The processor 760 may identify a signal applied from the front electrode 721, 723 to distinguish the charging signal from the bio-signal.

In steps 1213 and 1217, the processor 760 determines whether the interrupt is the first interrupt or the second interrupt on the basis of an analysis result. Steps 1213 and 1217 may be performed sequentially, in parallel, or in a reverse order.

If it is determined that the interrupt is the first interrupt in step 1213 (YES in operation 1213), the processor 760 processes a biometric information acquisition operation based on the on-demand measurement. For example, the processor 760 may process a bio-sensing operation based on the first sensor located in the front side 701. If a human body is in contact with the first sensor of the front side 701, the processor 760 may measure the biometric information. The front optic sensor 740 and the front electrode 721, 723 may be utilized in bio-sensing. The processor 760 may start the on-demand measurement when the bio-sensing is achieved, and may measure PPG, ECG, or BIA, by using the front electrode 721, 723 and the front optic sensor 740. The processor 760 may switch the first sensor of the front side 701 to a standby state after the on-demand measurement.

If it is determined that the interrupt is the second interrupt in step 1217 (NO in step 1217), the processor 760 simultaneously performs measuring and charging in step 1219. For example, the processor 760 may be switched to operate in a simultaneous mode for simultaneously performing the measuring and the charging. If a charging signal (e.g., a predetermined reference voltage or an electrical signal with a predetermined pattern) is applied to the front electrode 721, 723 of the front side 701, the processor 760 may enter the simultaneous mode for measuring and charging. In the simultaneous mode for measuring and charging, sufficient power may be supplied from an external device connected to the front electrode 721, 723, thereby setting a period of the always-on measurement to be short. Therefore, in the simultaneous mode for measuring and charging, the processor 760 may significantly improve accuracy of a health signal of the always-on measurement. While charging of the battery 785 by means of the front electrode 721, 723, when a reference voltage is not applied from the front electrode 721, 723 (e.g., when the charging module is detached), the first sensor of the front side 701 may be switched to the standby state.

If it is determined that the interrupt is not the first interrupt or the second interrupt in steps 1213 and 1217 (NO in step 1213, NO in step 1217), the processor 760 processes a corresponding operation in step 1221. For example, the processor 760 may determine that the interrupt is a simple malfunction, and may not be allowed to perform an operation for the interrupt (e.g., to ignore the interrupt). If it is determined that a voltage applied from the front electrode 721, 723 of the front side 701 is less than or equal to the reference voltage, the processor 760 may switch the first sensor of the front side 701 to the standby state.

Figure 13:
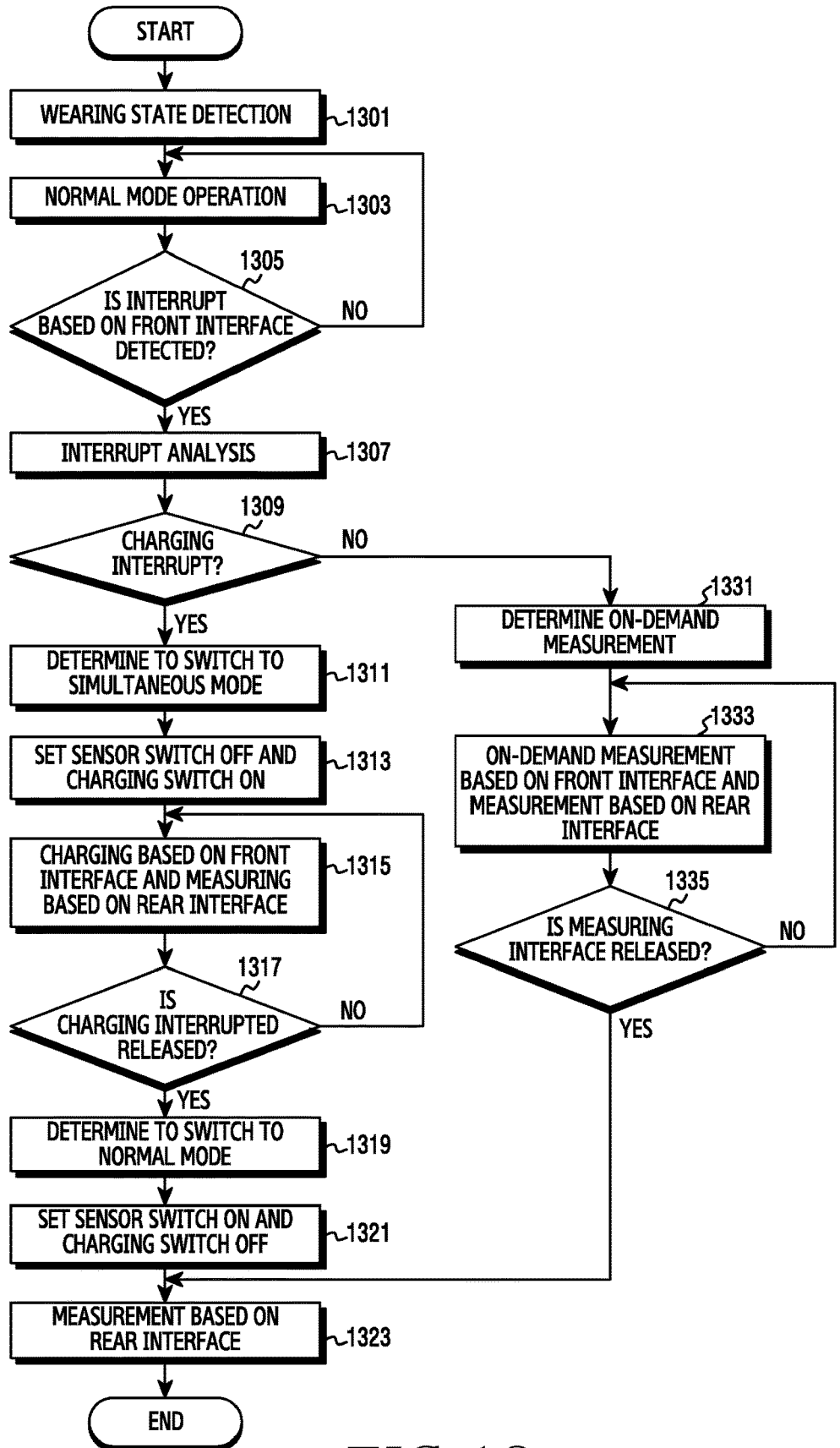
FIG. 13 is a flowchart illustrating a method of operating an electronic device, according to an embodiment of the present disclosure.

FIG. 13 is a flowchart illustrating a method of operating an electronic device according to an embodiment of the present disclosure.

Referring to FIG. 13, in step 1301, the processor 760 of the electronic device 700 detects a wearing state of the electronic device 700.

In step 1303, the processor 760 performs an operation based on a normal mode in response to detection of the wearing state of the electronic device 700.

In step 1305, the processor 760 determines whether an interrupt is detected by a front interface (e.g., the front electrode 721, 723 and the front optic sensor 740) located in the front side 701 of the electronic device 700. The processor 760 may determine whether a bio-signal or a charging signal is applied through the front electrode 721, 723 while operating based on the normal mode.

If the interrupt is not detected through the front interface in step 1305 (NO in step 1305), proceeding to step 1303, the processor 760 performs operations subsequent to step 1303. If the electronic device 700 is detached and a charging signal based on the rear electrode 731, 733 (or the charging electrode 791, 793) is detected while operating in the normal mode, the processor 760 may switch to the charging mode to process an operation based on the charging mode.

If the interrupt is detected through the front interface in step 1305 (YES in step 1305), the processor 760 analyzes the interrupt. For example, the processor 760 may analyze whether the interrupt is a charging interrupt or a measuring interrupt. The processor 760 may identify a signal applied from the front interface to distinguish the charging interrupt and the measuring interrupt. The processor 760 may determine the charging interrupt on the basis of an electric signal applied when an external device (e.g., a charging module) is mounted through the front electrode 721, 723, and may determine the measuring interrupt on the basis of a bio-signal applied by a user's touch through the front electrode 721, 723.

In step 1309, the processor 760 determines whether the interrupt is the charging interrupt or the measuring interrupt on the basis of an analysis result.

If it is determined that the interrupt is the charging interrupt in step 1309 (YES in step 1309), the processor 760 determines to switch to the simultaneous mode in step 1311. For example, the processor 760 may allow the electronic device 700 to switch to the simultaneous mode for simultaneously performing measuring and charging. The processor 760 may determine to switch to the simultaneous mode when a predetermined reference voltage or an electric signal with a predetermined pattern is applied to the front electrode 721, 723 of the front side 701.

In step 1313, the processor 760 provides control such that a sensor switch is set to be off and a charging switch is set to be on, on the basis of determining of the switching to the simultaneous mode. For example, for charging of the battery 731, 733 through the front electrode 721, 723, the processor 760 may disconnect a connection between the front electrode 721, 723 and a bio-sensor (e.g., the sensor controller 770), and may process a connection between the front electrode 721, 723 and the charging circuit (e.g., the battery charging module 780).

In step 1315, on the basis of switching to the simultaneous mode, the processor 760 processes a measurement based on a rear interface (e.g., the rear electrode 731, 733 and the rear optic sensor 745) while processing the charging based on the front interface. The processor 760 may include a measuring operation based on an enhanced mode (a precise mode) when a measurement is performed in the simultaneous mode. For example, on the basis of charging of the battery 731, 733, the processor 760 may set a measurement period based on the rear electrode 731, 733 to be short, may set a computation period of the processor 760 to be short, or may set persistency of a measurement time to be long, so as to acquire precise data for biometric information by changing at least one of those settings, thereby improving accuracy of a measurement.

The processor 760 may change persistency of a measurement period, computation period, or measurement time related to obtaining of the biometric information to a first setting in response to a low power mode (or a normal mode), and may obtain the biometric information according to the first setting by using at least one part of the front electrode 721, 723 or the rear electrode 731, 733. For example, the processor 760 may provide control to measure biometric information by setting the persistency of the measurement time to be short and/or the measurement period to be long according to the first setting.

The processor 760 may change the measurement period, computation period, or measurement time related to obtaining of the biometric information to a second setting in response to a precise mode (or an enhanced mode), and may obtain the biometric information according to the second setting by using the rear electrode 731, 733. For example, the processor 760 may provide control to measure the biometric information by setting the persistency of the measurement time to be long and/or the measurement period to be short according to the second setting.

In step 1317, the processor 760 determines whether to release the charging interrupt. The processor 760 may determine to release the charging interrupt on the basis of a detachment of an external device from the front interface.

If the release of the charging interrupt is not detected in step 1317 (NO in step 1317), proceeding to step 1315, the processor 760 processes operations subsequent to step 1315.

If the release of the charging interrupt is detected in step 1317 (YES in step 1317), the processor 760 determines to switch to a normal mode in step 1319. The processor 760 may determine to switch to the normal mode when a reference voltage or an electric signal with a predetermined pattern stops being applied to the front electrode 721, 723 of the front side 701 on the basis of the attachment/detachment of an external device.

In step 1321, the processor 760 provides control such that a sensor switch is set to be on and a charging switch is set to be off, on the basis of determining the switching to be the normal mode. For example, for an on-demand measurement through the front electrode 721, 723, the processor 760 may disconnect a connection between the front electrode 721, 723 and a charging circuit (e.g., the battery charging module 780), and may process a connection between the front electrode 721, 723 and a bio-sensor (e.g., the sensor controller 770).

In step 1323, on the basis of switching to the normal mode, the processor 760 processes the always-on measurement based on a rear interface. The processor 760 may process an on-demand measurement based on a front interface in the normal mode.

If it is determined that the interrupt is not the charging interrupt in step 1309 (NO in step 1309) on the basis of an analysis result and it is determined that the interrupt is a measuring interrupt, the processor 760 determines the on-demand measurement in step 1331.

In step 1333, on the basis of determining the on-demand measurement, the processor 760 simultaneously, independently, or selectively processes the measurement based on the rear interface while processing the measurement based on the front interface. When the on-demand measurement is performed based on the front interface, the processor 760 may process the measurement based on the rear interface in parallel or may not perform the measurement based on the rear interface. This may be performed distinctively according to a type of the on-demand measurement. If the same or similar type of measurements are performed by means of the front interface and the rear interface, the processor 760 may process the measurements in parallel or may stop the measurement based on the rear interface. If different types of measurements are performed by means of the front interface and the rear interface, the processor 760 may independently process the respective measurements.

If the electronic device 700 operates in the normal mode, the sensor switch and the charging switch may be set to be off in an initial operation. For example, the front electrode 721, 723 may be in a state of being disconnected from both a bio-sensor (e.g., the sensor controller 770) and a charging circuit (e.g., the PMIC 780). Such a state may be a setting for determining whether a user's touch is made using the front electrode 721, 723 or whether another device (e.g., a charging module) is mounted. In this case, for the on-demand measurement through the front electrode 721, 723, the processor 760 may include an operation of controlling a connection between the front electrode 721, 723 and the bio-sensor (e.g., the sensor controller 770).

In step 1335, the processor 760 determines whether to release the measuring interrupt. The processor 760 may determine the release of the measuring interrupt on the basis of the release of the user's touch from the front interface.

If the release of the measuring interrupt is not detected in step 1335 (NO in step 1335), proceeding to step 1333, the processor 760 processes operations subsequent to step 1333.

If the release of the measuring interrupt is detected in step 1335 (YES in step 1335), the processor 760 processes the always-on measurement based on the rear interface in step 1323.

In a scenario in which a connection between the front electrode 721, 723 and the bio-sensor (e.g., the sensor controller 770) is controlled for the on-demand measurement, the processor 760 may include an operation of setting a state of the sensor switch and the charging switch to an initial state. The processor 760 may set the sensor switch and the charging switch to be off, on the basis of the release of the measuring interrupt.

Figure 14A:
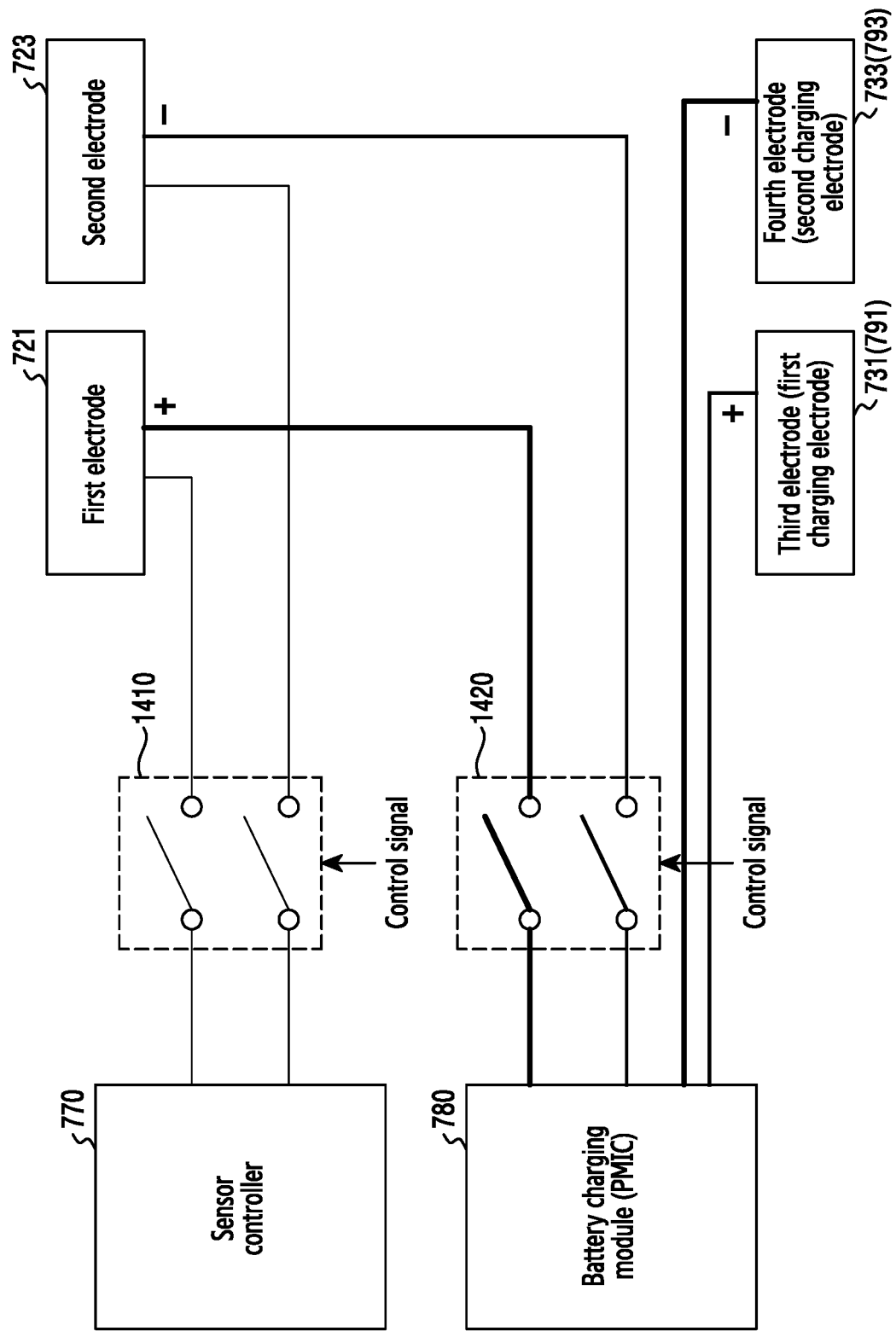
FIG. 14A, FIG. 14B, and FIG. 14C illustrate an operation for controlling a connection of a front electrode in an electronic device, according to an embodiment of the present disclosure.
Figure 14B:
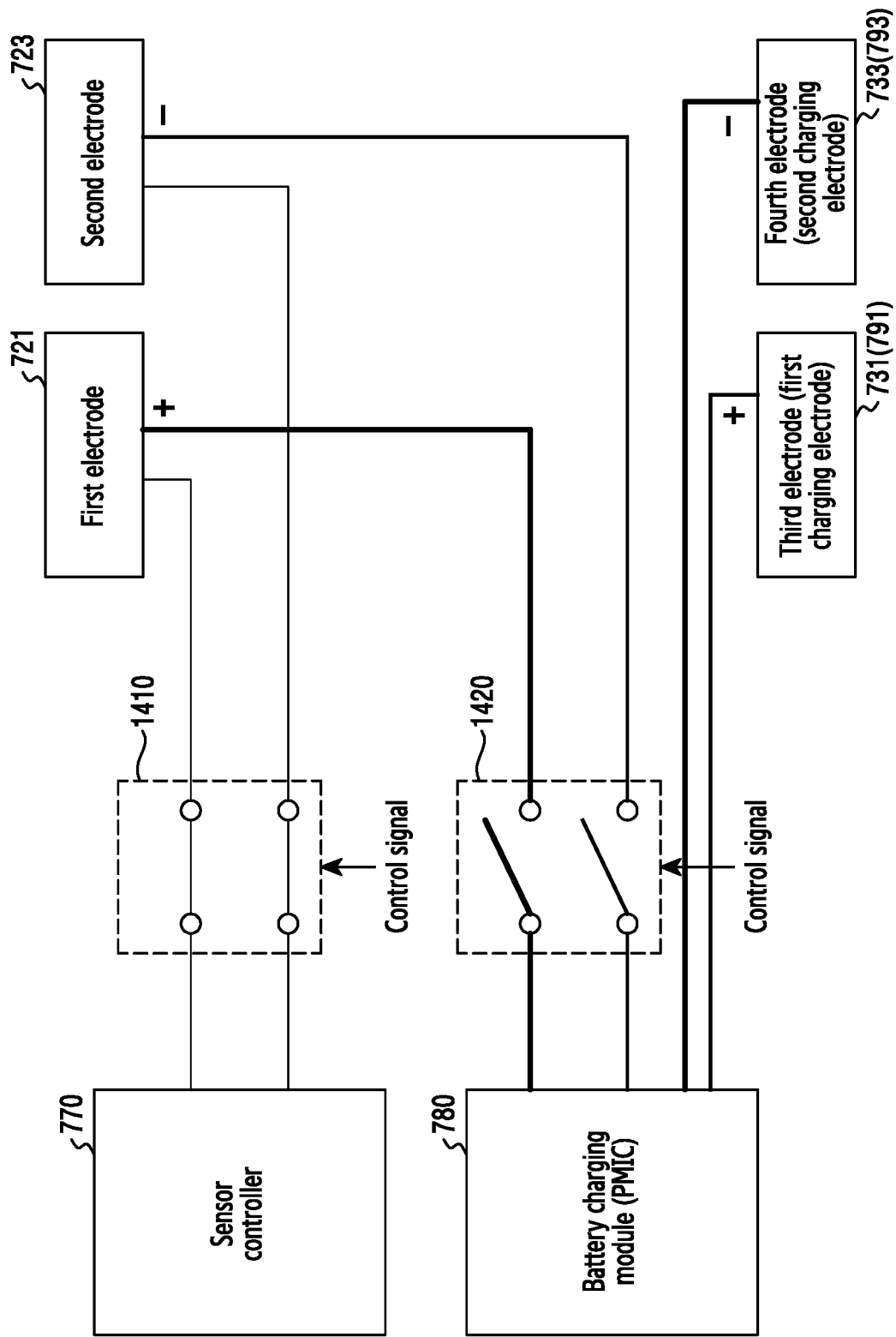
Figure 14C:
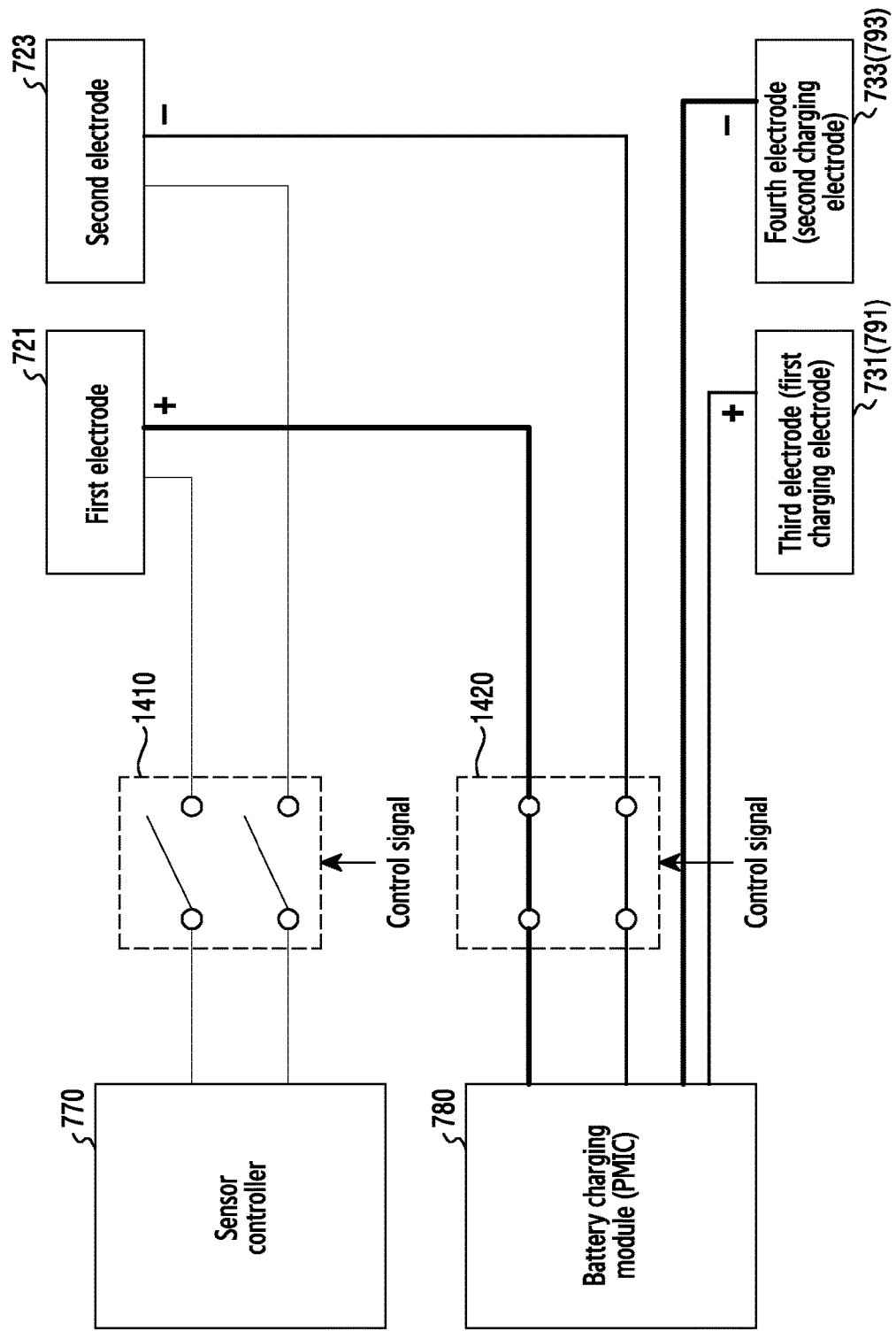

FIG. 14A, FIG. 14B, and FIG. 14C illustrate an operation for controlling a connection of a front electrode in an electronic device, according to embodiments of the present disclosure.

Referring to FIG. 14A, the front electrode (e.g., the first electrode 721 and the second electrode 723) located in the front side 701 of the electronic device 700 may be electrically connected to the sensor controller 770 or the battery charging module 780 on the basis of a switching control of a sensor switch 1410 and a charging switch 1420. The rear electrode (e.g., the third electrode 731 and the fourth electrode 733) located in the rear side 702 of the electronic device 700 may be in a state of being electrically connected to the battery charging module 780.

If the electronic device 700 operates in the normal mode, the sensor switch 1410 and the charging switch 1420 may be set by using a first method or a second method. In the first method, the initial state (e.g., a standby state of the first sensor) of the sensor switch 1410 and the charging switch 1420 is a state where the sensor switch 1410 is connected to the sensor controller 770 and the charging switch 1420 is disconnected from the battery charging module 780. In the second method, the initial state (e.g., the standby state of the first sensor) of the sensor switch 1410 and the charging switch 1420 may be a state where a connection between the sensor switch 1410 and the sensor controller 700 and a connection between the charging switch 1420 and the battery charging module 780 are both disconnected as shown in FIG. 14A. The second method may be a setting for determining whether a user's touch is made to use the front electrode 721, 723 or whether another device (e.g., a charging module) is mounted.

If a configured reference voltage (Vth) or a predefined signal is applied through the front electrode 721, 723, this may be recognized by the sensor controller 770, and the electronic device 700 may deliver a related signal to the processor 760. The processor 760 may determine to switch to the simultaneous mode for simultaneously performing measuring and charging in a measurement standby state (e.g., a normal mode) based on the front electrode 721, 723 of the front side 701.

The processor 760 may process an operation for connecting a path of the front electrode 721, 723 to the battery charging module 780 on the basis of determining to switch to the simultaneous mode. To switch to the simultaneous mode, the processor 760 may set the sensor switch 1410 to be off between the front electrode 721, 723 and the sensor controller 770 to disconnect a connection, and may set the charging switch 1420 to be on between the front electrode 721, 723 and the battery charging module 780 to charge a battery. The processor 760 may generate a control signal for controlling switching to each of the sensor switch 140 and the charging switch 1420.

FIG. 14B illustrates a case where the electronic device 700 operates in a normal mode. As shown in FIG. 14B, this may be a state where a path between the front electrode 721, 723 and the sensor controller 770 is connected, and a path between the front electrode 721, 723 and the battery charging module 780 is disconnected.

FIG. 14C illustrates a case where the electronic device 700 operates in a simultaneous mode. As shown in FIG. 14C, this may be a state where the path between the front electrode 721, 723 and the sensor controller 770 is disconnected, and the path between the front electrode 721, 723 and the battery charging module 780 is connected.

As shown in FIG. 10C, if a circuit for battery charging is configured through a connection between the front electrode 721, 723 and the battery charging module 780, a command may be delivered to the battery charging module 780 to start the charging. The battery charging module 780 may charge the battery 785 of the electronic device 700 by using power delivered through the front electrode (e.g., the first electrode 721 and the second electrode 723) located in the front side 701 on the basis of the command of the processor 780.

Charging may be performed through the front electrode 721, 723 in a state where the electronic device 700 is worn by the user.

Charging may be performed through the rear electrode (e.g., the third electrode 731 and the fourth electrode 733) or the charging electrode (e.g., the first charging electrode 791 and the second charging electrode 793), in a state where the electronic device 700 is not worn by the user (a non-wearing state).

When a configured reference voltage or a predefined signal is applied, the processor 760 may process an operation in a state where the rear electrode is charged through the rear electrode 731, 733 or the charging electrode 791, 793. In this state, if the charging module 910, 920 is connected to the front electrode 721, 723, the processor 760 may operate to charge not only the internal battery 785 but also the charging module 910, 920 by using power supplied from the rear electrode 731, 733. The processor 760 may control the front electrode 721, 723 to deliver the power supplied from the rear electrode 731, 733 to the charging module 910, 920. The charging module 910, 920 may independently perform charging through a wired or wireless connection while the electronic device 700 operates in the normal mode.

Figure 15:
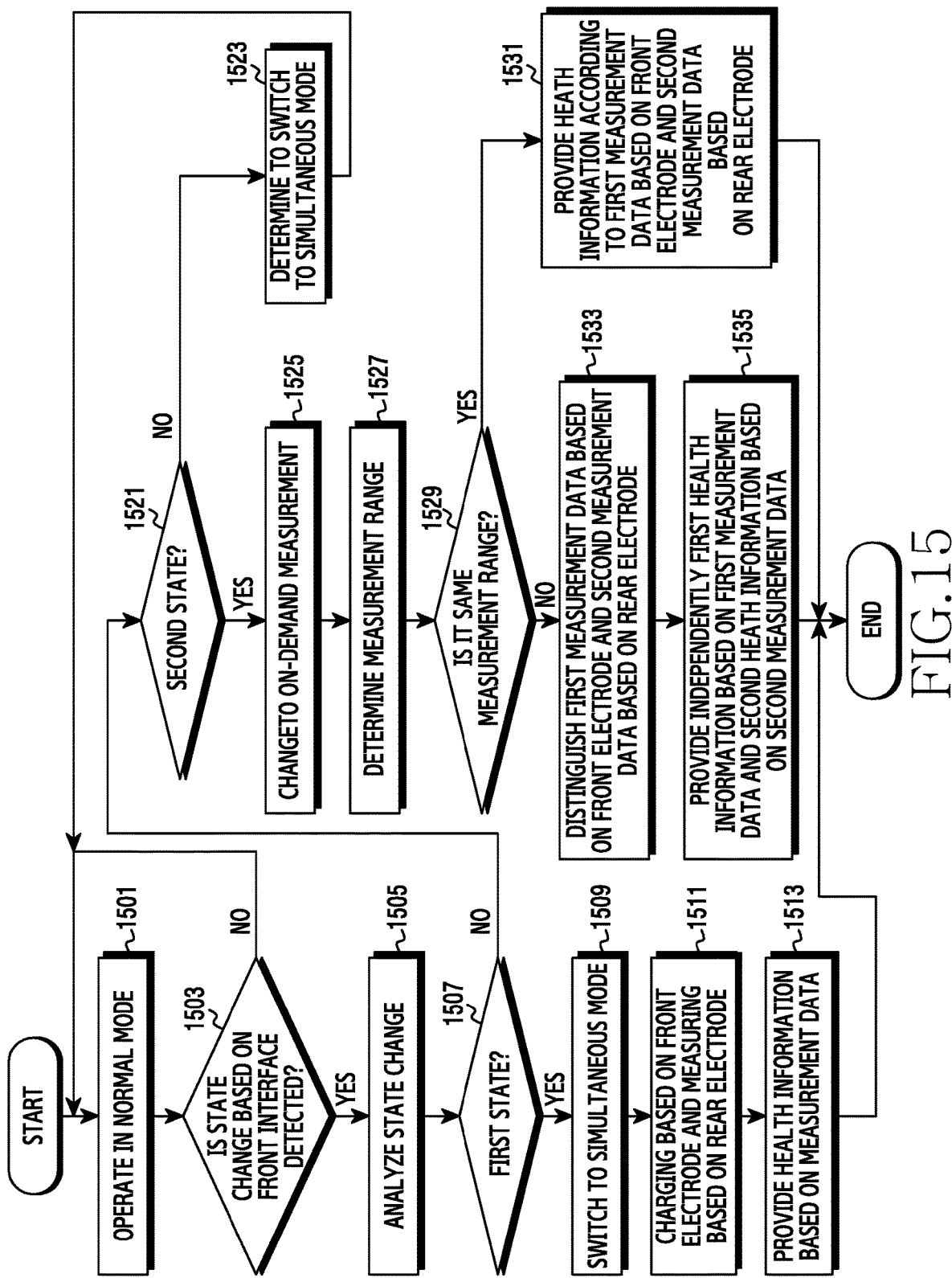
FIG. 15 illustrates a method of operating an electronic device, according to an embodiment of the present disclosure.

FIG. 15 is a flowchart illustrating a method of operating an electronic device according to an embodiment of the present disclosure.

Referring to FIG. 15, in step 1501, the processor 760 of the electronic device 700 operates in a normal mode. This may be a state where the electronic device 700 is worn by a user or a state where the processor 760 performs an operation based on the normal mode of the electronic device 700 as described above.

In step 1503, the processor 760 determines whether a state change based on the front electrode 721, 723 located in the front side 701 of the electronic device 700 is detected. The processor 760 may determine whether a bio-signal or a charging signal is applied through the front electrode 721, 723 while operating based on the normal mode.

If the state change is not detected through the front electrode 721, 723 in step 1503 (NO in step 1503), proceeding to step 1501, the processor 760 performs operations subsequent to step 1501. If the electronic device 700 is detached and a charging signal based on the rear electrode 731, 733 (or the charging electrode 791, 793) is detected while operating in the normal mode, the processor 760 may switch to the charging mode to process an operation based on the charging mode.

If the state change is detected through the front electrode 721, 723 in step 1503 (YES in step 1503), the processor 760 analyzes the state change. If a reference voltage (or an electric signal with a predefined pattern) or a bio-signal is applied through the front electrode 721, 723 located in the front side 701, the processor 760 may determine that the state change occurs. The processor 760 may analyze a type of state change based on a result of the determination. For example, the processor 760 may analyze whether the state change corresponds to a first state for charging the battery 785 using the front electrode 721, 723 or a second state for measuring a bio-signal using the front electrode 721, 723.

In steps 1507 and 1521, the processor 760 determines whether the state change is the first state or the second state on the basis of a result of the determination. Steps 1507 and 1521 may be performed sequentially, in parallel, or in a reverse order.

If it is determined that the state change is not the first state or the second state in steps 1507 and 1521 (NO in step 1507, NO in step 1521), the processor 760 ignores the state change in step 1523. For example, the processor 760 may determine that the state change based on the front electrode 721, 723 is a simple malfunction, and may not perform an operation for the state change.

If it is determined that the state change is the first state in step 1507 (YES in step 1507), the processor 760 switches an operation mode of the electronic device 700 from the normal mode to the simultaneous mode in step 1509. The simultaneous mode may include a mode for simultaneously performing charging based on the front electrode 721, 723 and measuring based on the rear electrode 731, 733.

In step 1511, the processor 760 processes a measurement based on the rear electrode 731, 733 while processing the charging based on the front electrode 721, 723 on the basis of switching to the simultaneous mode. The processor 760 may include a measuring operation based on an enhanced mode when performing the measurement in the simultaneous mode. For example, the processor 760 may set a measurement period based on the rear electrode 731, 733 to be short or may set a computation period of the processor 760 to be short, thereby increasing accuracy of a measurement by changing at least one of those settings.

In step 1513, the processor 760 provides health information on the basis of measurement data. The processor 760 may provide related health information through a video output (e.g., the display 750) or an audio output (e.g., the speaker 750) on the basis of the measurement data which is always measured through the rear electrode 731, 733.

If it is determined that the state change is the second state in step 1521 (YES in step 1521), the processor 760 determines an on-demand measurement based on the front electrode 721, 723 in step 1525.

In step 1527, the processor 760 determines a measurement range on the basis of determining the on-demand measurement. For example, the processor 760 may determine the measurement range of the front electrode 721, 723 and the rear electrode 731, 733 on the basis of information configured by the user. The processor 760 may compare a first measurement range configured for the on-demand measurement based on the front electrode 721, 723 and a second measurement range configured for the always-on measurement based on the rear electrode 731, 733. The measurement range may include information indicating a range (or type) of a biometric measurement to be performed by the user.

In step 1529, the processor 760 determines whether the first measurement range and the second measurement range are the same measurement range on the basis of a result of the determination. The processor 760 may determine whether the first measurement range based on the front electrode 721, 723 and the second measurement range based on the rear electrode 731, 733 are included in the same measurement range.

If the processor 760 determines that the first measurement range and the second measurement range are the same measurement range in step 1529 (YES in step 1529), then in step 1531, the processor 760 provides health information on the basis of first measurement data based on the front electrode 721, 723 and second measurement data based on the rear electrode 731, 733. The processor 760 may combine the first measurement data for the on-demand measurement through the front electrode 721, 723 and the second measurement data for the always-on measurement through the rear electrode 731, 733 or may correct the second measurement data by using first measurement, thereby providing related health information through those configured processes. The health related information may be provided to the user through a video output (e.g., the display 750) or an audio output (e.g., a speaker).

If it is determined that the first measurement range and the second measurement range are not the same measurement range in step 1529 (NO in step 1529), then in step 1533, the processor 760 distinguishes the first measurement data based on the front electrode 721, 723 and the second measurement data based on the rear electrode 731, 733. The processor 760 may determine the first measurement data and the second measurement data as independent data, and may operate to provide health information on the basis of each measurement data.

In step 1535, the processor 760 independently provides first health information based on the first measurement data and second health information based on the second measurement data. The processor 760 may configure the first health information on the basis of the first measurement data for the on-demand measurement through the front electrode 721, 723, and may configure the second health information on the basis of the second measurement data for the always-on measurement through the rear electrode 731, 733. The first health information and the second health information may be combined or individually provided to the user through the video output (e.g., the display 750) or the audio output (e.g., the speaker).

A method of operating an electronic device, according to an embodiment of the present disclosure, may include determining whether a battery is being charged through a charging circuit, if the battery is not being charged, acquiring biometric information by using a first method through a bio-sensor, and if the battery is being charged, acquiring the biometric information by using a second method through the bio-sensor.

According to an embodiment of the present disclosure, the electronic device may include a measuring circuit for inputting a signal by an external device or a user. The measuring circuit may include at least one front electrode located in a front side of the electronic device, and at least one rear electrode located in a rear side of the electronic device.

According to an embodiment of the present disclosure, the electronic device may include selectively connecting the measuring circuit to the charging circuit or the bio-sensor on the basis of whether the battery is being charged.

According to an embodiment of the present disclosure, the connecting may include, if the battery is not being charged, connecting the front electrode to the bio-sensor, and if the battery is being charged, connecting the front electrode to the charging circuit.

According to an embodiment of the present disclosure, the connecting may include detecting a charging signal related to charging of the battery through the front electrode, connecting the front electrode to the charging circuit on the basis of the detecting of the charging signal, and charging the battery by using the front electrode, and acquiring the biometric information by using the rear electrode.

According to an embodiment of the present disclosure, the first method may include changing persistency of a measurement period, computation period, or measurement time related to obtaining the biometric information according to a first setting in response to a low power mode, and obtaining the biometric information according to the first setting by using the front electrode or the rear electrode. The second method may include changing the measurement period, computation period, or measurement time related to obtaining the biometric information according to a second setting in response to a precise mode, and obtaining the biometric information according to the second setting by using the rear electrode.

According to an embodiment of the present disclosure, the connecting may include detecting a bio-signal through the front electrode, connecting the front electrode to the bio-sensor on the basis of the detected bio-signal, and acquiring the biometric information by using the front electrode and the rear electrode.

According to an embodiment of the present disclosure, the method may further include, if the battery is not being charged by using the measuring circuit, disconnecting a front electrode of the measuring circuit from the charging circuit and the bio-sensor in the standby state of the measuring circuit, detecting the interrupt through a front electrode of the measuring circuit in the standby state of the measuring circuit, and selectively connecting the front electrode to the charging circuit or the bio-sensor in response to the interrupt. The interrupt may include an interrupt corresponding to a user's touch on the measuring circuit in the standby state or mounting of an external device to the measuring circuit.

In an electronic device and an operating method thereof, according to various embodiments of the present disclosure, the electronic device can be charged without having to cancel (release) a state where a user wears the electronic device (e.g., a wrist-type wearable device). An original structure of an apparatus (device) for a biometric measurement can be utilized to perform charging without having to configure a separate charging port for charging in a state where the electronic device is worn.

According to various embodiments of the present disclosure, a user's biometric information can be continuously measured without interruption to provide more accurate health information. Since the electronic device is not necessarily detached from a user's body to charge the electronic device, a user's sleep state can be persistently monitored, thereby easily measuring a user's health state more accurately. A user can be less aware of charging the electronic device, and a service can be provided 24 hours a day, 7 days a week (e.g., a 24/7 service).

According to various embodiments of the present disclosure, the electronic device can contribute to improving a usability, convenience, or precise biometric measurement of the electronic device.

While the present disclosure has been shown and described with reference to certain embodiments, it will be understood by those skilled in the art that various changes in form and details may be made therein without departing from the spirit and scope of the present disclosure, which is defined, not by the detailed description and embodiments, but by the appended claims and their equivalents.

What is claimed is:

1. An electronic device comprising:
    a battery;
    front electrodes located in a front side of the electronic device,
    rear electrodes located in a rear side of the electronic device, wherein the front electrodes and the rear electrodes are for charging the battery and acquiring biometric information;
    a charging circuit configured to charge the battery;
    a sensor controller configured to measure the biometric information through the front and rear electrodes;
    a switch configured to selectively connect the front electrodes to the charging circuit and the sensor controller; and
    a processor configured to:
        determine whether a charging module is mounted to the front electrodes;
        if the charging module is not mounded to the front electrodes, control the switch to connect the front electrodes to the sensor controller and acquire the biometric information by using a first method; and
        if the charging module is mounted to the front electrodes, control the switch to connect the front electrodes to the charging circuit and acquire the biometric information by using a second method.

2. The electronic device of claim 1, wherein the processor is further configured to:
    detect a charging signal related to charging the battery through the front electrodes;
    control the switch to connect the front electrodes to the charging circuit based on the detected charging signal;
    charge the battery using the front electrodes; and
    acquire the biometric information using the rear electrodes.

3. The electronic device of claim 1, wherein the first method includes:
    changing persistency of a measurement period, a computation period, or a measurement time related to obtaining the biometric information according to a first setting in response to a low power mode, and
    obtaining the biometric information according to the first setting using the front electrodes or the rear electrodes, and
wherein the second method includes:
    changing the measurement period, the computation period, or the measurement time related to obtaining the biometric information according to a second setting in response to a precise mode, and
    obtaining the biometric information according to the second setting using the rear electrodes.

4. The electronic device of claim 1, wherein the processor is further configured to:
    detect a bio-signal through the front electrodes;
    connect the front electrodes to the sensor controller based on the detected bio-signal; and
    acquire the biometric information using the front electrodes and the rear electrodes.

5. The electronic device of claim 1, further comprising a measuring circuit configured to receive an input signal from an external device or a user,
    wherein the processor is further configured to set the measuring circuit to a standby state if the charging module is not mounted to the front electrodes, and
    wherein the measuring circuit is further configured to provide an interrupt corresponding to a user's touch in the standby state or mounting of the external device.

6. The electronic device of claim 5, wherein the processor is further configured to control the switch to disconnect the front electrodes from the charging circuit and the sensor controller in the standby state of the measuring circuit.

7. The electronic device of claim 6, wherein the processor is further configured to:
    detect the interrupt through the front electrodes in the standby state of the measuring circuit; and
    control the switch to selectively connect the front electrodes to the charging circuit or the sensor controller in response to the interrupt.

8. A method of operating an electronic device, the method comprising:
    measuring biometric information, by a sensor controller of the electronic device, through rear electrodes connected to the sensor controller, wherein the rear electrodes are located in a rear side of the electronic device;

determining whether a charging module is mounted to front electrodes, wherein the front electrodes are located in a front side of the electronic device;

in response to determining that the charging module is not mounted to the front electrodes, connecting, using a switch of the electrodes device, the front electrodes to the sensor controller and acquiring biometric information by using a first method; and in response to determining that the charging module is mounted to the front electrodes, connecting, by using the switch, the front electrodes to charging circuit and acquired the biometric information by using a second method, wherein the front electrodes and the rear electrodes are for charging a battery of the electronic device and acquiring the biometric information.

9. The method of claim 8, wherein connecting the front electrodes to the charging circuit comprises:

detecting a charging signal related to charging the battery through the front electrodes;

connecting the front electrodes to the charging circuit in response to detecting the charging signal;

charging the battery using the front electrodes; and acquiring the biometric information using the rear electrodes.

10. The method of claim 8, wherein the first method includes:

changing persistency of a measurement period, a computation period, or a measurement time related to obtaining the biometric information according to a first setting in response to a low power mode, and obtaining the biometric information according to the first setting using the front electrodes or the rear electrodes, and wherein the second method includes:

changing the measurement period, the computation period, or the measurement time related to obtaining the biometric information according to a second setting in response to a precise mode, and obtaining the biometric information according to the second setting using the rear electrodes.

11. The method of claim 8, wherein connecting the first electrodes to the sensor controller comprises:

detecting a bio-signal through the front electrodes;

connecting the front electrodes to the sensor controller based on the detected bio-signal; and acquiring the biometric information using the front electrodes and the rear electrodes.

12. The method of claim 8, wherein the electronic device includes a measuring circuit for receiving an input signal from an external device or a user, wherein the method further comprises:

in response to determining that the charging module is not mounted to the front electrodes, disconnecting the front electrodes from the charging circuit and the sensor controller in a standby state of the measuring circuit;

detecting an interrupt through the front electrodes in the standby state of the measuring circuit; and selectively connecting the front electrodes to the charging circuit or the sensor controller in response to the interrupt, and wherein the interrupt corresponds to a user's touch in the standby state or mounting of the external device.

* * * * *